(12) United States Patent
Ishii et al.

(10) Patent No.: US 10,831,001 B2
(45) Date of Patent: Nov. 10, 2020

(54) IMAGING OPTICAL SYSTEM

(71) Applicant: NALUX CO., LTD., Osaka-shi, Osaka (JP)

(72) Inventors: Kenta Ishii, Osaka (JP); Daisuke Seki, Osaka (JP)

(73) Assignee: NALUX CO., LTD., Osaka (JP)

(*) Notice: Subject to any disclaimer, the term of this patent is extended or adjusted under 35 U.S.C. 154(b) by 107 days.

(21) Appl. No.: 16/164,038

(22) Filed: Oct. 18, 2018

(65) Prior Publication Data

US 2019/0049704 A1 Feb. 14, 2019

Related U.S. Application Data

(63) Continuation of application No. PCT/JP2016/064127, filed on May 12, 2016.

(51) Int. Cl.
*G02B 13/04* (2006.01)
*A61B 1/00* (2006.01)
(Continued)

(52) U.S. Cl.
CPC .......... *G02B 13/04* (2013.01); *A61B 1/00096* (2013.01); *G02B 9/12* (2013.01); *G02B 13/0035* (2013.01); *G02B 23/243* (2013.01)

(58) Field of Classification Search
CPC ...... G02B 13/04; G02B 13/0035; G02B 9/12; G02B 23/243; A61B 1/00096
(Continued)

(56) References Cited

U.S. PATENT DOCUMENTS 8,130,456 B2 * 3/2012 Asami ........................ 359/753
2005/0225872 A1 10/2005 Uzawa et al.
(Continued)

FOREIGN PATENT DOCUMENTS

EP 1 526 398 A1 4/2005
EP 1 777 941 A1 4/2007
(Continued)

OTHER PUBLICATIONS

Nov. 22, 2019 Extended Search Report issued in European Patent Application No. 16901668.0.
(Continued)

*Primary Examiner* — Evelyn A Lester
(74) *Attorney, Agent, or Firm* — Squire Patton Boggs (US) LLP

(57) ABSTRACT

The imaging optical system is provided with a first lens having a negative refractive power, a second lens having a positive refractive power, an aperture stop, and a third lens having a positive refractive power, disposed from the object side to the image side. With |d| being the distance between the image-side principal point of the first lens and the object-side principal point of the second lens, d=−|d| being the signed distance between the image-side principal point of the first lens and the object-side principal point of the second lens when the image-side principal point of the first lens is further towards the image side than the object-side principal point of the second lens, and f12 being the composite focal length of the first lens and the second lens, the relationships d<0 and 0.005<d/f12<16 are established.

7 Claims, 15 Drawing Sheets

(51) Int. Cl.
    *G02B 9/12*      (2006.01)
    *G02B 13/00*     (2006.01)
    *G02B 23/24*     (2006.01)

(58) Field of Classification Search
    USPC ............................... 359/716, 740, 753, 784
    See application file for complete search history.

(56) References Cited

U.S. PATENT DOCUMENTS

| | | |
|---|---|---|
| 2007/0091458 A1 | 4/2007 | Asami et al. |
| 2008/0068729 A1 | 3/2008 | Asami |
| 2008/0130128 A1 | 6/2008 | Yamashita et al. |
| 2009/0080089 A1 | 3/2009 | Hirose |
| 2015/0080662 A1 | 3/2015 | Harada |

FOREIGN PATENT DOCUMENTS

| | | |
|---|---|---|
| EP | 1 903 369 A1 | 3/2008 |
| JP | 06-34878 A | 2/1994 |
| JP | 10-170821 A | 6/1998 |
| JP | 2004151295 A | 5/2004 |
| JP | 2004-337346 A | 12/2004 |
| JP | 2005-181596 A | 7/2005 |
| JP | 2006-162829 A | 6/2006 |
| JP | 2006-220691 A | 8/2006 |
| JP | 2007-025499 A | 2/2007 |
| JP | 2007-114546 A | 5/2007 |
| JP | 2008-102500 A | 5/2008 |
| JP | 2009-075315 A | 4/2009 |
| JP | 2009-098322 A | 5/2009 |
| JP | 2015-060019 A | 3/2015 |

OTHER PUBLICATIONS

International Search Report & Written Opinion dated Jul. 26, 2016 corresponding to International Patent Application No. PCT/JP2016/064127, and partial English translation thereof.
Office Action dated Nov. 15, 2016 corresponding to Japanese Patent Application No. 2016-551870.

* cited by examiner

IMAGING OPTICAL SYSTEM

CROSS REFERENCE TO RELATED APPLICATION

This is a Continuation of International Patent Application No. PCT/JP2016/064127 filed May 12, 2016.

BACKGROUND

Technical Field

The present invention relates to an imaging optical system, particularly to an imaging optical system for endoscopes.

Description of the Related Art

Endoscopes used in the medical field include insertion type ones and capsule type ones. In ordinary insertion type endoscopes, an imaging optical system at the front end portion, that is, an objective lens and an image sensor located at a distance are connected to each other by a fiber or a relay lens. In the imaging optical system for such ordinary insertion type endoscopes, telecentricity is required in order to minimize optical loss. Further, in insertion type endoscopes, there exist electronic ones in which an imaging optical system and an image sensor are provided at the front end portion and an image is displayed on a display located at a distance. Capsule type endoscopes are provided with an imaging optical system and an image sensor in the capsule. Accordingly, in the imaging optical system for capsule type endoscopes and electronic endoscopes, telecentricity is not required. On the other hand, any types of endoscopes are required to be compact, of wide-angle and of high-resolution. Aberrations of the optical system has to be made smaller in order to be of high-resolution.

On the other hand, imaging optical systems for endoscopes of prior art have the following problems.

Patent document 1 (JP2015-060019) discloses an objective lens for endoscopes, in which, from the object side to the image side, a lens having a negative refractive power, an aperture stop, a lens having a positive refractive power and a lens having a positive refractive power are arranged. Aberrations are corrected to a sufficient extent by the two lenses having positive refractive powers and located between the aperture stop and the image plane. On the other hand, since the aperture stop is placed between the first lens and the second lens, the distance between the principal points of the first lens and the second lens cannot be reduced. Accordingly, a sufficiently wide angle of view cannot be obtained.

Patent document 2 (JP2004-337346) discloses an objective lens for endoscopes, in which, from the object side to the image side, a lens having a negative refractive power, a lens having a positive refractive power, an aperture stop and a lens having a positive refractive power are arranged. The distance between the principal points of the first lens and the second lens is great, and the angle of view is not sufficiently wide. Additionally, in order to obtain a compact and wide-angle imaging lens unit, sapphire is used as the lens material, and therefore the lens unit is costly.

Patent document 3 (JPH10-170821) discloses an objective lens for endoscopes, in which, from the object side to the image side, a lens having a negative refractive power, a lens having a positive refractive power, an aperture stop and a lens having a positive refractive power are arranged. The angle of view is relatively wide, but importance is attached to telecentricity, and therefore aberrations cannot be corrected to a sufficient extent.

Thus, an imaging optical system for realizing endoscopes that are sufficiently compact, sufficiently of wide-angle and sufficiently of high-resolution has not been developed.

PRIOR ART DOCUMENTS

Patent Documents

Patent document 1: JP2015-060019
Patent document 2: JP2004-337346
Patent document 3: JPH10-170821

Accordingly, there is a need for an imaging optical system for realizing endoscopes that are sufficiently compact, sufficiently of wide-angle and sufficiently of high-resolution. The object of the invention is to provide an imaging optical system for realizing an endoscope that is sufficiently compact, sufficiently of wide-angle and sufficiently of high-resolution.

SUMMARY OF INVENTION

An imaging optical system according to the present invention includes a first lens having a negative refractive power, a second lens having a positive refractive power, an aperture stop and a third lens having a positive refractive power, which are arranged from the object side to the image side. When distance between the image-side principal point of the first lens and the object-side principal point of the second lens is represented by $|d|$, signed distance is represented by $d=-|d|$ when the image-side principal point of the first lens is located closer to the image than the object-side principal point of the second lens, and the composite focal length of the first lens and the second lens is represented by f12, the relationships $$d<0 \tag{1}$$

and $$0.005<d/f12<16 \tag{2}$$

are established.

The layout in which a first lens having a negative refractive power, a second lens having a positive refractive power and a third lens having a positive refractive power are arranged from the object side to the image side allows aberrations in a wide angle to be easily corrected. In order to attach a greater importance to making the system compact, of wide-angle and of high-resolution than to increasing telecentricity, the aperture stop should preferably be placed between the second lens and the third lens.

In order to determine refractive powers of the first and second lenses such that the diameter of the first lens does not become too great and a sufficiently great angle of view can be obtained, Expression (2) should preferably be satisfied. If d/f12 is equal to or less than the lower limit of Expression (2), the angle of view cannot be made sufficiently wide when the first lens has a small diameter, and if d/f12 is equal to or greater than the upper limit of Expression (2), aberrations cannot be corrected to a sufficient extent, and a high resolution cannot be obtained when the first lens has a small diameter.

In general, the composite refractive power $\phi_{12}$ of a lens having a refractive power $\phi_1$ and a lens having a refractive power $\phi_2$ can be expressed according to the paraxial theory by the following equation.

$$\phi_{12}=\phi_1+\phi_2-\phi_1\phi_2 d$$

The refractive power of the first lens is negative, and the refractive power of the second lens is positive, and therefore the product $\phi_1\phi_2$ of the refractive power of the first lens and the refractive power of the second lens is negative. Accordingly, if d is negative, $-\phi_1\phi_2 d$ becomes negative, and the composite refractive power $\phi_{12}$ is apt to become negative. Accordingly, in order to make the composite refractive power $\phi_{12}$ strongly negative, it is advantageous to satisfy Expression (1).

With an imaging optical system according to the present invention, an endoscope that is sufficiently compact, sufficiently of wide-angle and sufficiently of high-resolution can be realized.

In an imaging optical system according to a first embodiment of the present invention, the relationship $$0.1 < d/f12 < 6 \qquad (2)'$$

is established.

With an imaging optical system according to the present embodiment, a higher resolution can be obtained.

In an imaging optical system according to a second embodiment of the present invention, the relationship $$0.12 < d/f2 < 0.15 \qquad (2)''$$

is established.

According to the present embodiment, the imaging optical system can be further downsized, and a still higher resolution of the imaging optical system can be obtained.

In an imaging optical system according to a third embodiment of the present invention, when the common principal axis of the first lens, the second lens and the third lens is defined as the optical axis, distance between the point on the optical axis and on the image-side surface of the third lens and the image plane is represented by t3, and distance between the point on the optical axis and on the object-side surface of the first lens and the point on the optical axis and on the image-side surface of the third lens is represented by t, the relationship $$t3/t > 0.5$$

is established.

According to the present embodiment, a sufficiently great sensor size can be obtained despite compactness of the imaging optical system, and a sufficiently great space can be provided between the sensor and the lens, which is advantageous to the assembly.

In an imaging optical system according to a fourth embodiment of the present invention, when the common principal axis of the first lens, the second lens and the third lens is defined as the optical axis, the point on the optical axis and on the object-side surface of the second lens is located closer to the object than the point on the image-side surface of the first lens, through which the outermost light ray of a light beam corresponding to the angle of view passes.

With the layout of the present embodiment, the total lens length as well as aberrations generated by the image-side surface of the first lens having a negative refractive power can be reduced.

In an imaging optical system according to a fifth embodiment of the present invention, when Abbe constant of the material of which the first lens is made is represented by $\nu 1$, Abbe constant of the material of which the second lens is made is represented by $\nu 2$ and Abbe constant of the material of which the third lens is made is represented by $\nu 3$, the relationships $$\nu 1 > \nu 2$$

$$\nu 3 > \nu 2$$

are established.

According to the present embodiment, chromatic aberrations are well corrected.

In an imaging optical system according to a sixth embodiment of the present invention, when image height of the light beam corresponding to the angle of view is represented by y, and the effective diameter of the first lens is represented by D, the relationship $$0.75 < 2 \times y/D < 1.25$$

is established.

With the present embodiment, by determining the ratio of the effective diameter of the first lens to the sensor size in an appropriate range, the imaging optical system can be downsized, and aberrations of the imaging optical system can be corrected to a sufficient extent so that a high resolution can be realized.

An imaging optical system according to a seventh embodiment of the present invention is used for endoscopes.

DESCRIPTION OF EMBODIMENTS

Figure 1:
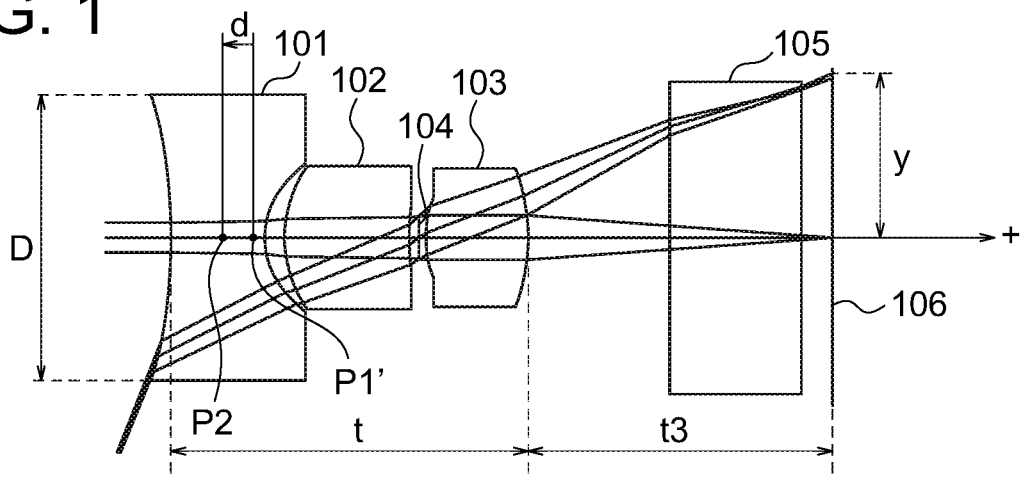
FIG. 1 shows a layout of the imaging optical system according to Example 1.

FIG. 1 shows a layout of an imaging optical system according to an embodiment (that is Example 1 to be described later) of the present invention. The imaging optical system includes a first lens 101 having a negative refractive power, a second lens 102 having a positive refractive power, an aperture stop 104 and a third lens 103 having a positive refractive power, which are arranged from the object side to the image side. Light beams that pass through the above-described lenses pass through an optical member 105 and are focused on an image plane 106. The optical member 105 is a cover glass for a sensor or the like. In the text of specification and claims, a lens having a negative refractive power means a lens having a negative refractive power for paraxial rays, and a lens having a positive refractive power means a lens having a positive refractive power for paraxial rays.

Features of the imaging optical systems according to the present invention will be described below.

The first feature of the imaging optical systems according to an embodiment of the present invention is to include a first lens having a negative refractive power, a second lens having a positive refractive power, an aperture stop and a third lens having a positive refractive power, which are arranged from the object side to the image side. The layout in which a first lens having a negative refractive power, a second lens having a positive refractive power and a third lens having a positive refractive power are arranged from the object side to the image side allows aberrations in a wide angle to be easily corrected. From the viewpoint of increasing telecentricity, it is advantageous to place the aperture stop between the first lens and the second lens. From the viewpoint of making the system compact, of wide-angle and of high-resolution, it is advantageous to place the aperture stop between the second lens and the third lens. In the present invention, a greater importance is attached to making the system compact, of wide-angle and of high-resolution than to increasing telecentricity, and therefore the aperture stop is placed between the second lens and the third lens.

The second feature of the imaging optical systems according to an embodiment of the present invention is to satisfy the following conditions.

$$d<0 \tag{1}$$

$$0.005<d/f12<16 \tag{2}$$

In the above-described expressions, d represents signed distance between the image-side principal point of the first lens and the object-side principal point of the second lens. The absolute value of d represents distance between the image-side principal point of the first lens and the object-side principal point of the second lens, the positive sign of d signifies that the image-side principal point of the first lens is located closer to the object than the object-side principal point of the second lens, and the negative sign of d signifies that the image-side principal point of the first lens is located closer to the image than the object-side principal point of the second lens. Further, f12 represents the composite focal length of the first lens and the second lens.

In general, in layouts of many wide-angle lenses, a retrofocus type is employed, in which a lens having a negative refractive power and a lens having a positive refractive power are arranged respectively on the object side and on the image side. As this fact shows, a lens having a strongly negative refractive power located on the object side is advantageous to making the angle of view wider.

On the other hand, when a strongly negative refractive power is assigned to the first lens alone, the diameter of the first lens becomes too great. When the diameter of the first lens becomes too great, the imaging optical system, and by extension, the endoscope cannot be downsized. In order to determine refractive powers of the first and second lenses such that the diameter of the first lens does not become too great and a sufficiently wide angle of view can be obtained, Expression (2) should preferably be satisfied. If d/f12 is equal to or less than the lower limit of Expression (2), the angle of view cannot be made sufficiently wide when the first lens has a small diameter, and if d/f12 is equal to or greater than the upper limit of Expression (2), aberrations cannot be corrected to a sufficient extent, and a high resolution cannot be obtained when the first lens has a small diameter.

If the following condition is satisfied, a higher resolution of the imaging optical system can be obtained.

$$0.1<d/f12<6 \tag{2'}$$

If the following condition is satisfied, the imaging optical system can be further downsized, and a still higher resolution of the imaging optical system can be obtained.

$$0.12<d/f2<0.15 \tag{2''}$$

In general, the composite refractive power $\phi_{12}$ of a lens having a refractive power $\phi_1$ and a lens having a refractive power $\phi_2$ can be expressed according to the paraxial theory by the following equation.

$$\phi_{12}=\phi_1+\phi_2-\phi_1\phi_2 d$$

As described above, the refractive power of the first lens is negative, and the refractive power of the second lens is positive, and therefore the product $\phi_1\phi_2$ of the refractive power of the first lens and the refractive power of the second lens is negative. Accordingly, if d is negative, $-\phi_1\phi_2 d$ becomes negative, and the composite refractive power $\phi_{12}$ is apt to become negative. Accordingly, in order to make the composite refractive power $\phi_{12}$ strongly negative, it is advantageous to satisfy Expression (1).

The third feature of the imaging optical systems according to an embodiment of the present invention is to satisfy the following condition.

$$t3/t>0.5 \tag{3}$$

When the common principal axis of the first lens, the second lens and the third lens is defined as the optical axis, t3 represents distance between the point on the optical axis and on the image-side surface of the third lens and the image plane, and t represents distance between the point on the optical axis and on the object-side surface of the first lens and the point on the optical axis and on the image-side surface of the third lens in the above-described expressions.

In general, a wide-angle lens has a short focal length, and therefore distance between the lens closest to the image and the image plane is small. In the imaging optical systems according to embodiments of the present invention, a strongly negative refractive power is assigned to the lens on the object side, as described as the first feature, and therefore distance between the lens surface closest to the image and the image plane is relatively great. Particularly, when the condition of Expression (3) is satisfied, a sufficiently great sensor size can be obtained despite compactness of the imaging optical system, and a sufficiently great space can be provided between the sensor and the lens, which is advantageous to the assembly.

The fourth feature of the imaging optical systems according to an embodiment of the present invention is that when the common principal axis of the first lens, the second lens and the third lens is defined as the optical axis, the point on the optical axis and on the object-side surface of the second lens is located closer to the object than the point on the image-side surface of the first lens, through which the outermost light ray of a light beam corresponding to the angle of view passes.

In the layout of the fourth feature, the vertex of the object-side surface of the second lens is placed in the space bordered by the image-side surface of the first lens. The above-described layout can reduce the total lens length as well as aberrations generated by the image-side surface of the first lens having a negative refractive power.

The fifth feature of the imaging optical systems according to an embodiment of the present invention is to satisfy the following conditions.

$$v1 > v2 \quad (4)$$

$$v3 > v2 \quad (5)$$

In the above-described expressions, v1 represents Abbe constant of the material of which the first lens is made, v2 represents Abbe constant of the material of which the second lens is made and v3 represents Abbe constant of the material of which the third lens is made.

In the case of a three-lens layout in which the first lens has a negative refractive power, the second lens has a positive refractive power and the third lens has a positive refractive power, chromatic aberrations can be best corrected when the Abbe constant of the second lens is the lowest.

The sixth feature of the imaging optical systems according to an embodiment of the present invention is to satisfy the following condition.

$$0.75 < 2xy/D < 1.25 \quad (6)$$

In the above-described expression, y represents image height of the light beam corresponding to the angle of view, and D represents the effective diameter of the first lens.

In order to downsize a system in which a sensor and an imaging optical system is combined, the effective diameter of the first lens has to be made small. On the other hand, if the effective diameter of the first lens is made too small for the sensor size, aberrations cannot be corrected to a sufficient extent in the imaging optical system, and resolution cannot be increased to a sufficient extent. Accordingly, the ratio between 2xy that corresponds to the sensor size and D should preferably satisfy Expression (6). If the ratio between 2xy and D is equal to or smaller than the lower limit of Expression (6), the system cannot be downsized to a sufficient extent. On the other hand, if the ratio between 2xy and D is equal to or greater than the upper limit of Expression (6), the lens diameter is too small for the sensor size so that the correction of aberrations cannot be performed to a sufficient extent.

Examples of the present invention will be described below.

The material of the first lens is cycloolefin polymer (grade: E48R) in the examples except Example 5. The material of the first lens of Example 5 is cycloolefin polymer (grade: 330R). The material of the second lens is polycarbonate (grade: SP1516). The material of the third lens is cycloolefin polymer (grade: E48R). The material of the plate (which is to be used as a cover glass for the sensor) located on the object side of the sensor is N-BK7.

Each surface of the respective lenses and the optical member can be expressed by the following expression.

$$z = \frac{r^2/R}{1 + \sqrt{1 - (1+k)r^2/R^2}} + \sum_{i=1} A_i r^i \quad (7)$$

The straight line connecting the centers of curvature of the two surfaces of the first lens, the second lens and the third lens is defined as a z axis. z represents a coordinate along the z axis defining the position of a point on each lens surface with reference to the point of intersection of each surface with the z axis where z is positive on the image side of the point of intersection. r represents distance from the z axis to the point on each lens surface. R is signed radius of curvature at the vertex of each surface, that is, signed radius of curvature at the center of curvature. The absolute value of R is radius of curvature at the vertex of each surface, that is, radius of curvature at the center of curvature. The sign is positive when the lens surface is convex toward the object side and is negative when the lens surface is convex toward the image side. k is the conic constant. Ai is an aspheric coefficient. i is an integer.

The common principal axis of the first lens, the second lens and the third lens is defined as the optical axis.

Aberrations of the imaging optical system of each example for the F line (wavelength: 486.1 nm), the d line (wavelength: 587.56 nm) and the C line (wavelength: 656.27 nm) are shown.

In the tables given below, the unit of length of "radius of curvature" and "space" is millimeter.

Example 1

FIG. 1 shows a layout of the imaging optical system according to Example 1. The imaging optical system includes a first lens 101 having a negative refractive power, a second lens 102 having a positive refractive power, an aperture stop 104 and a third lens 103 having a positive refractive power, which are arranged from the object side to the image side. Light beams that pass through the above-described lenses pass through an optical member 105 and are focused on an image plane 106. The optical member 105 is a cover glass for a sensor or the like. FIG. 1 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from the surface of the object that is 15 mm distant from the first lens along the optical axis.

In FIGS. 1, 4, 7, 10, 13, 17, 20, 23, 25 and 28, d, t, t3, D and y are shown. In the drawings P1' shows the position of the image-side principal point of the first lens, and P2 shows the object-side principal point of the second lens. As recited in claim 1, d is negative when P1' is closer to the image than P2.

TABLE 1

| # | Radius of curvature | Space | Refractive index | Abbe constant | K |
|---|---|---|---|---|---|
| Object | Infinity | 1.50E+01 | | | 0.00000E+00 |
| 1 | −1.58E+00 | 2.88E−01 | 1.5312 | 56.0 | 0.00000E+00 |
| 2 | 2.61E−01 | 6.03E−02 | | | −3.48643E−01 |
| 3 | 3.89E−01 | 3.85E−01 | 1.6141 | 25.3 | −1.40865E+00 |
| 4 | 8.07E−01 | 2.95E−02 | | | −2.00000E+00 |
| Aperture stop | Infinity | 2.07E−02 | | | 0.00000E+00 |
| 6 | 3.91E−01 | 3.14E−01 | 1.5312 | 56.0 | −5.50000E+00 |
| 7 | −5.13E−01 | 4.33E−01 | | | 7.12229E−02 |
| 8 | Infinity | 4.05E−01 | 1.5168 | 64.2 | 0.00000E+00 |
| 9 | Infinity | 1.00E−01 | | | 0.00000E+00 |

Table 2 shows aspheric coefficients of Expression (7) for surface 1 to surface 4 and surface 6 to surface 9.

TABLE 2

| # | A2 | A4 | A6 | A8 | A10 |
|---|---|---|---|---|---|
| Object | 0.00000E+00 | 0.00000E+00 | 0.00000E+00 | 0.00000E+00 | 0.00000E+00 |
| 1 | 0.00000E+00 | 3.27010E−02 | 8.07148E−02 | 9.45205E−03 | 0.00000E+00 |
| 2 | 0.00000E+00 | 2.20988E+00 | −2.74909E+01 | −1.31064E+01 | 0.00000E+00 |
| 3 | 0.00000E+00 | 3.14383E+00 | −1.54876E+01 | −1.22233E+01 | 0.00000E+00 |
| 4 | 0.00000E+00 | −3.88796E+00 | −7.26608E+02 | 1.18448E+04 | 0.00000E+00 |
| Aperture stop | 0.00000E+00 | 0.00000E+00 | 0.00000E+00 | 0.00000E+00 | 0.00000E+00 |
| 6 | 0.00000E+00 | −7.90355E+00 | 8.19983E+02 | 1.09217E+04 | 0.00000E+00 |
| 7 | 0.00000E+00 | 1.46685E+00 | 4.42827E+01 | −3.59695E+00 | 0.00000E+00 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

Table 1 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 101, the image-side surface of the first lens 101, the object-side surface of the second lens 102 and the image-side surface of the second lens 102. Surface 6 to surface 9 respectively represent the object-side surface of the third lens 103, the image-side surface of the third lens 103, the object-side surface of the plate 105 and the image-side surface of the plate 105. Radius of curvature in the line of object represents radius of curvature of the object surface, and "infinity" shows that the object surface is a plane that is perpendicular to the optical axis. Space in the line of object represents distance from the object surface to the object-side surface of the first lens 101. In the line of surface 1, radius of curvature represents signed radius of curvature at the center of curvature of the object-side surface of the first lens 101 (R of Expression (7)), space represents thickness of the first lens 101, refractive index represents refractive index of the material of the first lens 101, Abbe constant represents Abbe constant of the material of the first lens 101 and k represents the conic constant of Expression (7) of the object-side surface of the first lens 101. In the line of surface 2, radius of curvature represents signed radius of curvature at the center of curvature of the image-side surface of the first lens 101 (R of Expression (7)), space represents the space between the image-side surface of the first lens 101 and the object-side surface of the second lens 102 and k represents the conic constant of Expression (7) of the image-side surface of the first lens 101. Ditto with the succeeding lines.

Figure 2:
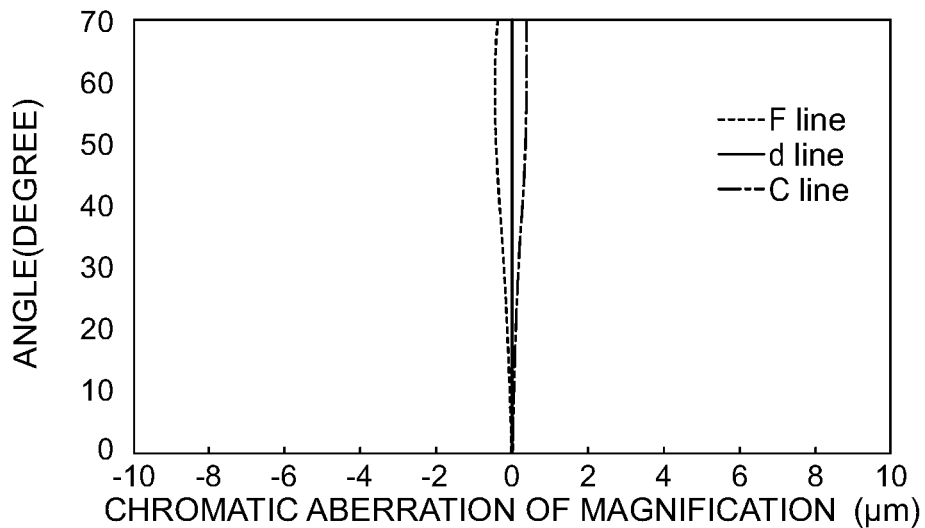
FIG. 2 shows chromatic aberrations of magnification of the imaging optical system according to Example 1.

FIG. 2 shows chromatic aberrations of magnification of the imaging optical system according to Example 1. The horizontal axis of FIG. 2 indicates chromatic aberrations of magnification of the F line and the C line with respect to the d line. The vertical axis of FIG. 2 indicates angle of the principal ray to the optical axis of a light beam that enters the imaging optical system. The maximum value of angle of the vertical axis corresponds to the half value of the angle of view.

Figure 3:
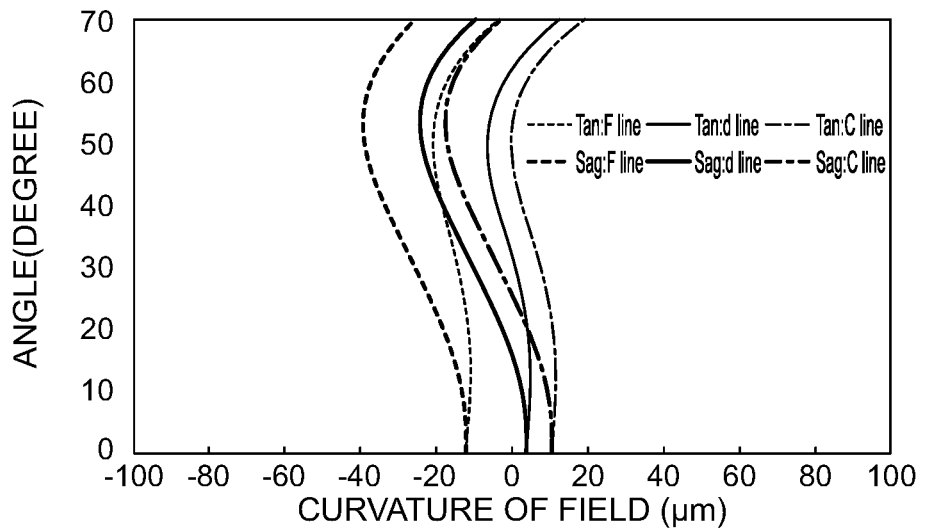
FIG. 3 shows curvature of field of the imaging optical system according to Example 1.

FIG. 3 shows curvature of field of the imaging optical system according to Example 1. The horizontal axis of FIG. 3 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 3 indicates angle of the principal ray to the optical axis of a light beam that enters the imaging optical system. The maximum value of angle of the vertical axis corresponds to the half value of the angle of view.

Example 2

Figure 4:
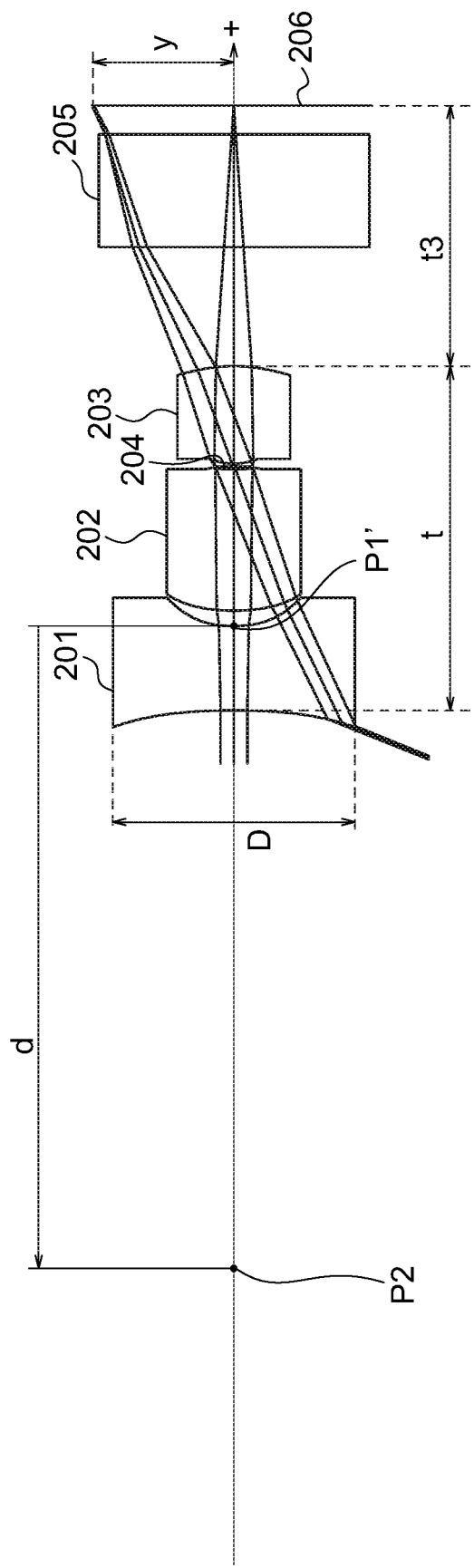
FIG. 4 shows a layout of the imaging optical system according to Example 2

FIG. 4 shows a layout of the imaging optical system according to Example 2. The imaging optical system includes a first lens 201 having a negative refractive power, a second lens 202 having a positive refractive power, an aperture stop 204 and a third lens 203 having a positive refractive power, which are arranged from the object side to the image side. Light beams that pass through the above-described lenses pass through an optical member 205 and are focused on an image plane 206. The optical member 205 is a cover glass for a sensor or the like. FIG. 4 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from the surface of the object that is 15 mm distant from the first lens along the optical axis.

Table 3 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 201, the image-side surface of the first lens 201, the object-side surface of the second lens 202 and the image-side surface of the second lens 202. Surface 6 to surface 9 respectively represent the object-side surface of the third lens 203, the image-side surface of the third lens 203, the object-side surface of the plate 205 and the image-side surface of the plate 205. Radius of curvature in the line of object represents radius of curvature of the object surface, and "infinity" shows that the object surface is a plane that is perpendicular to the optical axis. Space in the line of object represents distance from the object surface to the object-side surface of the first lens 201. In the line of surface 1, radius of curvature represents signed radius of curvature at the center of curvature of the object-side surface of the first lens 201 (R of Expression (7)), space represents thickness of the first lens 201, refractive index represents refractive index of the material of the first lens 201, Abbe constant represents Abbe constant of the material of the first lens 201 and k represents the conic constant of Expression (7) of the object-side surface of the first lens 201.

In the line of surface 2, radius of curvature represents signed radius of curvature at the center of curvature of the image-side surface of the first lens 201 (R of Expression (7)), space represents the space between the image-side surface of the first lens 201 and the object-side surface of the second lens 202 and k represents the conic constant of Expression (7) of the image-side surface of the first lens 201. Ditto with the succeeding lines.

TABLE 3

| # | Radius of curvature | Space | Refractive index | Abbe constant | K |
|---|---|---|---|---|---|
| Object | Infinity | 1.50E+01 | | | 0.00E+00 |
| 1 | −4.18E+01 | 3.00E−01 | 1.5312 | 56.0 | 1.00E+02 |
| 2 | 3.54E−01 | 5.65E−02 | | | −7.68E−01 |
| 3 | 7.30E−01 | 5.10E−01 | 1.6141 | 25.3 | 1.88E+00 |
| 4 | 6.30E−01 | 9.60E−03 | | | 2.84E+01 |
| Aperture stop | Infinity | 9.42E−03 | | | 0.00E+00 |
| 6 | 2.97E−01 | 3.51E−01 | 1.5312 | 56.0 | −9.72E+00 |
| 7 | −5.87E−01 | 4.33E−01 | | | −2.24E+01 |
| 8 | Infinity | 4.05E−01 | 1.5168 | 64.2 | 0.00E+00 |
| 9 | Infinity | 1.00E−01 | | | 0.00E+00 |

Table 4A and Table 4B show aspheric coefficients of Expression (7) for surface 1 to surface 4 and surface 6 to surface 9.

TABLE 4A

| # | A2 | A4 | A6 | A8 | A10 |
|---|---|---|---|---|---|
| Object | 0.00000E+00 | 0.00000E+00 | 0.00000E+00 | 0.00000E+00 | 0.00000E+00 |
| 1 | 0.00000E+00 | −3.15665E+00 | 8.05514E+00 | 1.65046E+01 | −71.4776E+01 |
| 2 | 0.00000E+00 | 2.20411E−01 | −1.21651E+00 | −4.86361E+01 | 2.51042E+03 |
| 3 | 0.00000E+00 | 1.74433E+00 | 8.33808E+01 | −2.50380E+03 | 1.78157E+04 |
| 4 | 0.00000E+00 | 4.02267E+00 | −1.53210E+04 | 2.59258E+06 | −4.54464E+07 |
| Aperture stop | 0.00000E+00 | 0.00000E+00 | 0.00000E+00 | 0.00000E+00 | 0.00000E+00 |
| 6 | 0.00000E+00 | 4.62584E+01 | −6.43882E+03 | 4.26465E+05 | 2.17810E+07 |
| 7 | 0.00000E+00 | −9.22228E+00 | 9.14832E+01 | 4.09901E+03 | −5.47297E+04 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

TABLE 4B

| # | A12 | A14 |
|---|---|---|
| Object | 0.00000E+00 | 0.00000E+00 |
| 1 | −7.24613E+00 | −1.62249E+01 |
| 2 | 2.45222E+03 | 0.00000E+00 |
| 3 | −9.56947E+03 | 0.00000E+00 |
| 4 | −2.10880E+10 | 0.00000E+00 |
| Aperture stop | 0.00000E+00 | 0.00000E+00 |
| 6 | −2.84689E+09 | 0.00000E+00 |
| 7 | 2.05339E+05 | −1.00190E+07 |
| 8 | 0.00000E+00 | 0.00000E+00 |
| 9 | 0.00000E+00 | 0.00000E+00 |

Figure 5:
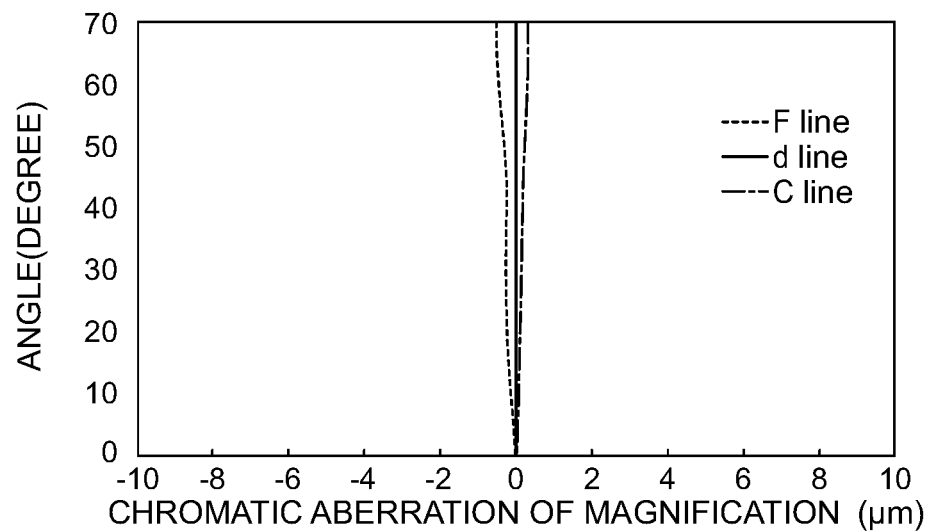
FIG. 5 shows chromatic aberrations of magnification of the imaging optical system according to Example 2.

FIG. 5 shows chromatic aberrations of magnification of the imaging optical system according to Example 2. The horizontal axis of FIG. 5 indicates chromatic aberrations of magnification of the F line and the C line with respect to the d line. The vertical axis of FIG. 5 indicates angle of the principal ray to the optical axis of a light beam that enters the imaging optical system. The maximum value of angle of the vertical axis corresponds to the half value of the angle of view.

Figure 6:
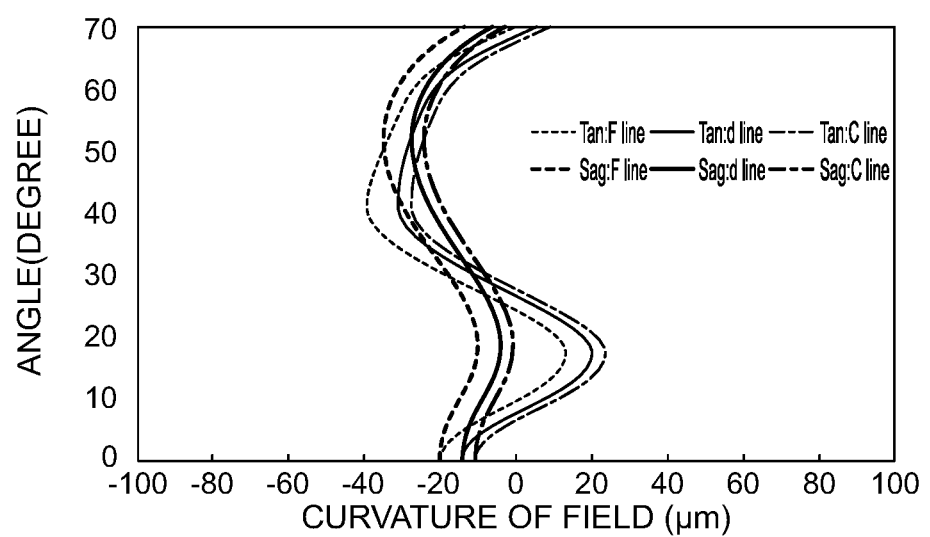
FIG. 6 shows curvature of field of the imaging optical system according to Example 2.

FIG. 6 shows curvature of field of the imaging optical system according to Example 2. The horizontal axis of FIG. 6 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 6 indicates angle of the principal ray to the optical axis of a light beam that enters the imaging optical system. The maximum value of angle of the vertical axis corresponds to the half value of the angle of view.

Example 3

Figure 7:
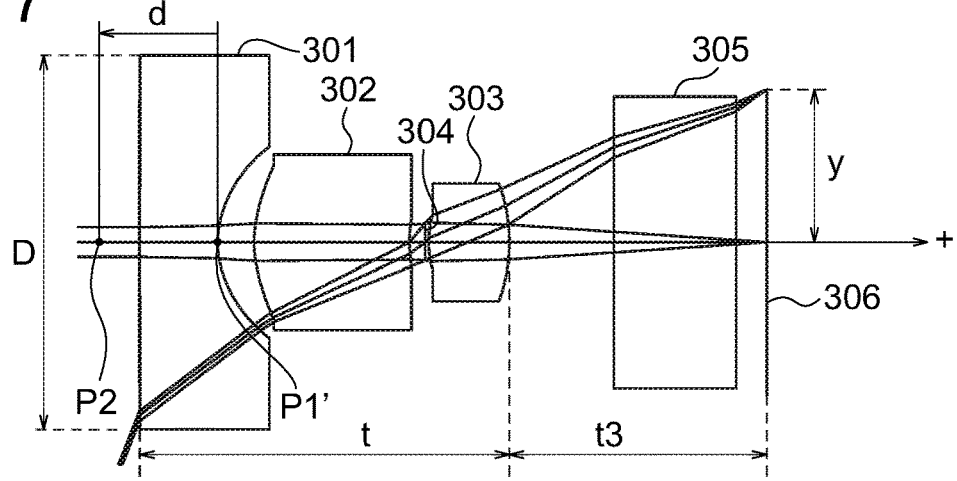
FIG. 7 shows a layout of the imaging optical system according to Example 3.

FIG. 7 shows a layout of the imaging optical system according to Example 3. The imaging optical system includes a first lens 301 having a negative refractive power, a second lens 302 having a positive refractive power, an aperture stop 304 and a third lens 303 having a positive refractive power, which are arranged from the object side to the image side. Light beams that pass through the above-described lenses pass through an optical member 305 and are focused on an image plane 306. The optical member 305 is a cover glass for a sensor or the like. FIG. 7 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from the surface of the object that is 15 mm distant from the first lens along the optical axis.

Table 5 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 301, the image-side surface of the first lens 301, the object-side surface of the second lens 302 and the image-side surface of the second lens 302. Surface 6 to surface 9 respectively represent the object-side surface of the third lens 303, the image-side surface of the third lens 303, the object-side surface of the plate 305 and the image-side surface of the plate 305. Radius of curvature in the line of object represents radius of curvature of the object surface, and "infinity" shows that the object surface is a plane that is perpendicular to the optical axis. Space in the line of object represents distance from the object surface to the object-side surface of the first lens 301. In the line of surface 1, radius of curvature represents signed radius of curvature at the center of curvature of the object-side surface of the first lens 301 (R of Expression (7)), space represents thickness of the first lens 301, refractive index represents refractive index of the material of the first lens 301, Abbe constant represents Abbe constant of the material of the first lens 301 and k represents the conic constant of Expression (7) of the object-side surface of the first lens 301. In the line of surface 2, radius of curvature represents signed radius of curvature at the center of curvature of the image-side surface of the first lens 301 (R of Expression (7)), space represents the space between the image-side surface of the first lens 301 and the object-side surface of the second lens 302 and k represents the conic constant of Expression (7) of the image-side surface of the first lens 301. Ditto with the succeeding lines.

TABLE 5

| # | Radius of curvature | Space | Refractive index | Abbe constant | K |
|---|---|---|---|---|---|
| Object | Infinity | 1.50E+01 | | | 0.00000E+00 |
| 1 | Infinity | 2.61E−01 | 1.5312 | 56.0 | 0.00000E+00 |
| 2 | 3.11E−01 | 1.25E−01 | | | −2.46070E−01 |
| 3 | 3.97E−01 | 5.22E−01 | 1.6141 | 25.3 | −2.13794E+00 |
| 4 | 4.54E−01 | 5.40E−02 | | | 0.00000E+00 |
| Aperture stop | Infinity | 1.06E−02 | | | 0.00000E+00 |
| 6 | 3.37E−01 | 2.72E−01 | 1.5312 | 56.0 | 0.00000E+00 |
| 7 | −5.53E−01 | 3.53E−01 | | | −1.43609E+00 |
| 8 | Infinity | 4.05E−01 | 1.5168 | 64.2 | 0.00000E+00 |
| 9 | Infinity | 1.00E−01 | | | 0.00000E+00 |

Table 6 shows aspheric coefficients of Expression (7) for surface 1 to surface 4 and surface 6 to surface 9.

TABLE 6

| # | A2 | A4 | A6 | A8 | A10 |
|---|---|---|---|---|---|
| Object | 0.00000E+00 | 0.00000E+00 | 0.00000E+00 | 0.00000E+00 | 0.00000E+00 |
| 1 | 0.00000E+00 | 0.00000E+00 | 0.00000E+00 | 0.00000E+00 | 0.00000E+00 |
| 2 | 0.00000E+00 | −5.78964E+00 | 8.20363E+00 | 1.91062E+01 | −1.07961E+03 |
| 3 | 0.00000E+00 | −2.69566E+00 | 1.36799E+00 | −1.72782E+01 | −2.27429E+03 |
| 4 | 0.00000E+00 | −1.28481E+01 | −3.08681E+03 | 1.62521E+05 | −2.40748E+06 |
| Aperture stop | 0.00000E+00 | 0.00000E+00 | 0.00000E+00 | 0.00000E+00 | 0.00000E+00 |
| 6 | 0.00000E+00 | −5.74703E+00 | −1.04201E+04 | 1.93862E+06 | −1.10746E+08 |
| 7 | 0.00000E+00 | −2.49331E+00 | −1.21983E+02 | 4.32087E+03 | −2.19281E+04 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

Figure 8:
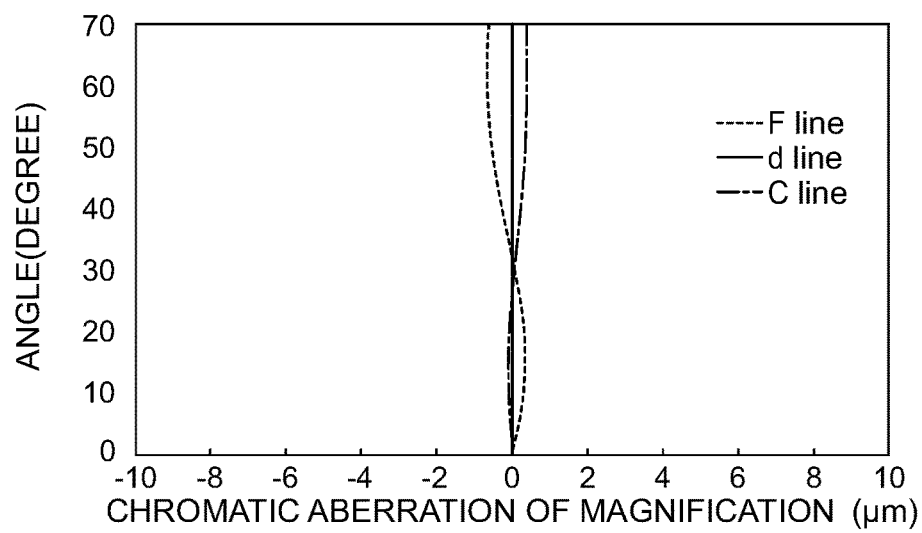
FIG. 8 shows chromatic aberrations of magnification of the imaging optical system according to Example 3.

FIG. 8 shows chromatic aberrations of magnification of the imaging optical system according to Example 3. The horizontal axis of FIG. 8 indicates chromatic aberrations of magnification of the F line and the C line with respect to the d line. The vertical axis of FIG. 8 indicates angle of the principal ray to the optical axis of a light beam that enters the imaging optical system. The maximum value of angle of the vertical axis corresponds to the half value of the angle of view.

Figure 9:
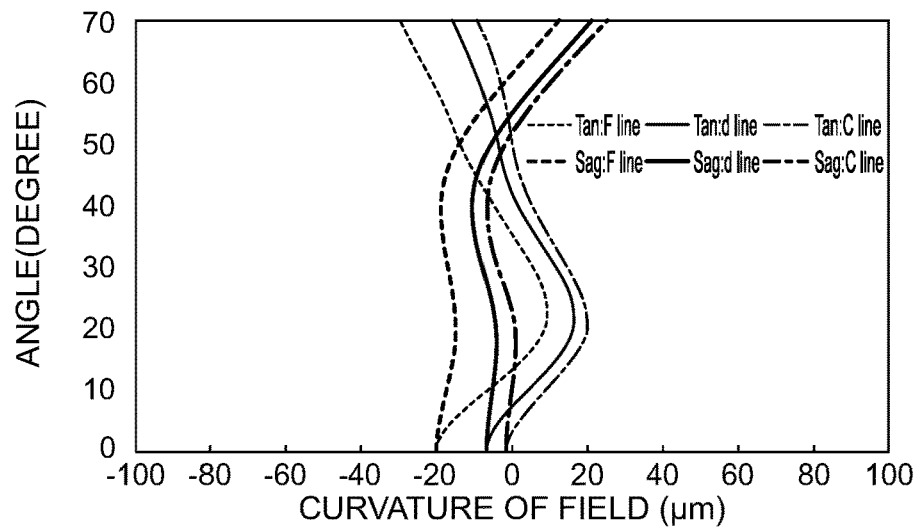
FIG. 9 shows curvature of field of the imaging optical system according to Example 3.

FIG. 9 shows curvature of field of the imaging optical system according to Example 3. The horizontal axis of FIG. 9 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 9 indicates angle of the principal ray to the optical axis of a light beam that enters the imaging optical system. The maximum value of angle of the vertical axis corresponds to the half value of the angle of view.

Example 4

Figure 10:
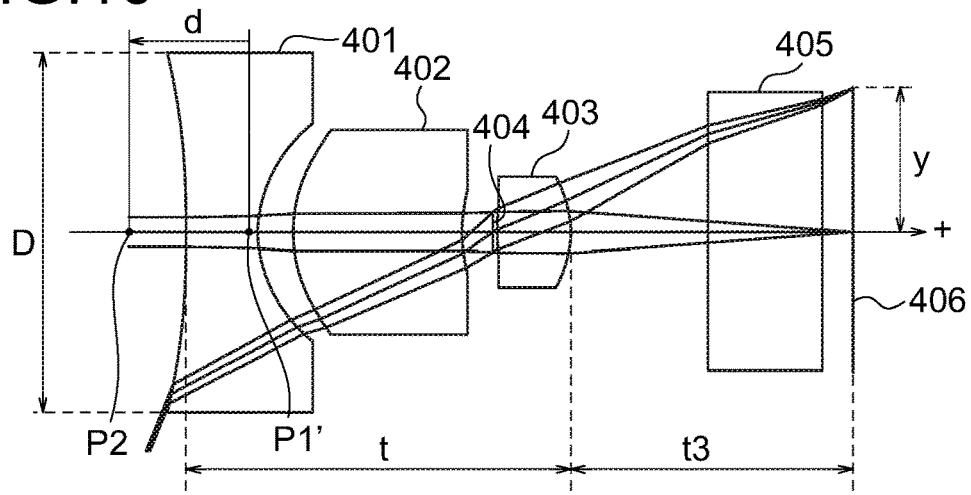
FIG. 10 shows a layout of the imaging optical system according to Example 4.

FIG. 10 shows a layout of the imaging optical system according to Example 4. The imaging optical system includes a first lens 401 having a negative refractive power, a second lens 402 having a positive refractive power, an aperture stop 404 and a third lens 403 having a positive refractive power, which are arranged from the object side to the image side. Light beams that pass through the above-described lenses pass through an optical member 405 and are focused on an image plane 406. The optical member 405 is a cover glass for a sensor or the like. FIG. 10 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from the surface of the object that is 15 mm distant from the first lens along the optical axis.

Table 7 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 401, the image-side surface of the first lens 401, the object-side surface of the second lens 402 and the image-side surface of the second lens 402. Surface 6 to surface 9 respectively represent the object-side surface of the third lens 403, the image-side surface of the third lens 403, the object-side surface of the plate 405 and the image-side surface of the plate 405. Radius of curvature in the line of object represents radius of curvature of the object surface, and "infinity" shows that the object surface is a plane that is perpendicular to the optical axis. Space in the line of object represents distance from the object surface to the object-side surface of the first lens 401. In the line of surface 1, radius of curvature represents signed radius of curvature at the center of curvature of the object-side surface of the first lens 401 (R of Expression (7)), space represents thickness of the first lens 401, refractive index represents refractive index of the material of the first lens 401, Abbe constant represents Abbe constant of the material of the first lens 401 and k represents the conic constant of Expression (7) of the object-side surface of the first lens 401. In the line of surface 2, radius of curvature represents signed radius of curvature at the center of curvature of the image-side surface of the first lens 401 (R of Expression (7)), space represents the space between the image-side surface of the first lens 401 and the object-side surface of the second lens 402 and k represents the conic constant of Expression (7) of the image-side surface of the first lens 401. Ditto with the succeeding lines.

TABLE 7

| # | Radius of curvature | Space | Refractive index | Abbe constant | K |
|---|---|---|---|---|---|
| Object | Infinity | 1.50E+01 | | | 0.00000E+00 |
| 1 | −3.00E+00 | 2.50E−01 | 1.5312 | 56.0 | 0.00000E+00 |
| 2 | 5.14E−01 | 1.25E−01 | | | 1.27534E−01 |
| 3 | 5.53E−01 | 5.99E−01 | 1.6141 | 25.3 | −9.71850E−01 |
| 4 | 6.77E−01 | 1.12E−01 | | | 0.00000E+00 |
| Aperture stop | Infinity | 1.00E−02 | | | 0.00000E+00 |
| 6 | 9.98E−01 | 2.63E−01 | 1.5312 | 56.0 | 0.00000E+00 |
| 7 | −3.71E−01 | 4.84E−01 | | | 3.41833E−01 |
| 8 | Infinity | 4.05E−01 | 1.5168 | 64.2 | 0.00000E+00 |
| 9 | Infinity | 1.00E−01 | | | 0.00000E+00 |

Table 8 shows aspheric coefficients of Expression (7) for surface 1 to surface 4 and surface 6 to surface 9.

TABLE 8

| # | A2 | A4 | A6 | A8 | A10 |
|---|---|---|---|---|---|
| Object | 0.00000E+00 | 0.00000E+00 | 0.00000E+00 | 0.00000E+00 | 0.00000E+00 |
| 1 | 0.00000E+00 | 0.00000E+00 | 0.00000E+00 | 0.00000E+00 | 0.00000E+00 |
| 2 | 0.00000E+00 | −5.11739E−03 | 0.00000E+00 | 0.00000E+00 | 0.00000E+00 |
| 3 | 0.00000E+00 | 2.68582E−01 | 0.00000E+00 | 0.00000E+00 | 0.00000E+00 |
| 4 | 0.00000E+00 | −8.19885E−01 | 0.00000E+00 | 0.00000E+00 | 0.00000E+00 |
| Aperture stop | 0.00000E+00 | 0.00000E+00 | 0.00000E+00 | 0.00000E+00 | 0.00000E+00 |
| 6 | 0.00000E+00 | −6.52170E+00 | 0.00000E+00 | 0.00000E+00 | 0.00000E+00 |
| 7 | 0.00000E+00 | −1.39959E−02 | 0.00000E+00 | 0.00000E+00 | 0.00000E+00 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

Figure 11:
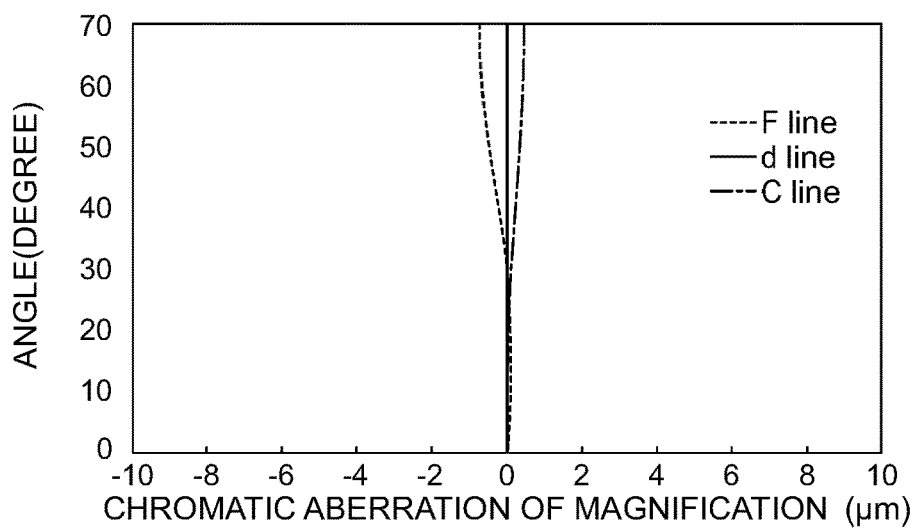
FIG. 11 shows chromatic aberrations of magnification of the imaging optical system according to Example 4.

FIG. 11 shows chromatic aberrations of magnification of the imaging optical system according to Example 4. The horizontal axis of FIG. 11 indicates chromatic aberrations of magnification of the F line and the C line with respect to the d line. The vertical axis of FIG. 11 indicates angle of the principal ray to the optical axis of a light beam that enters the imaging optical system. The maximum value of angle of the vertical axis corresponds to the half value of the angle of view.

Figure 12:
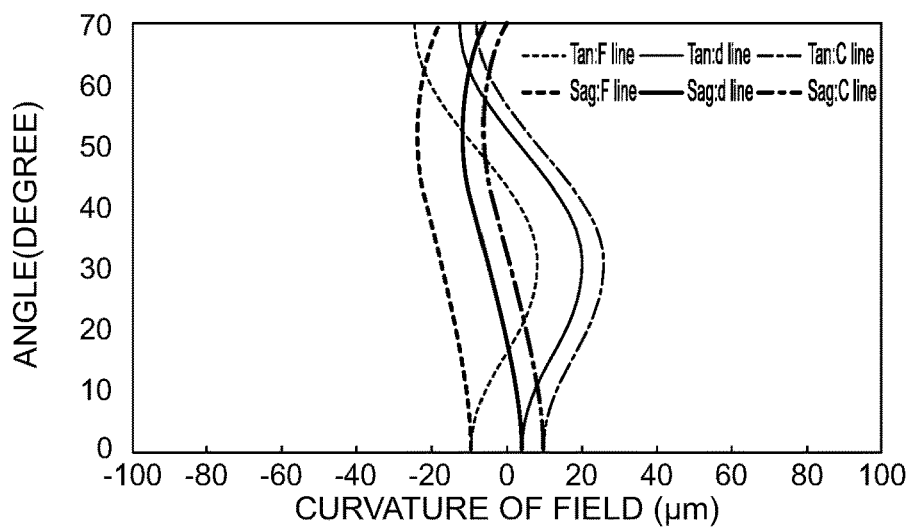
FIG. 12 shows curvature of field of the imaging optical system according to Example 4.

FIG. 12 shows curvature of field of the imaging optical system according to Example 4. The horizontal axis of FIG. 12 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 12 indicates angle of the principal ray to the optical axis of a light beam that enters the imaging optical system. The maximum value of angle of the vertical axis corresponds to the half value of the angle of view.

Example 5

Figure 13:
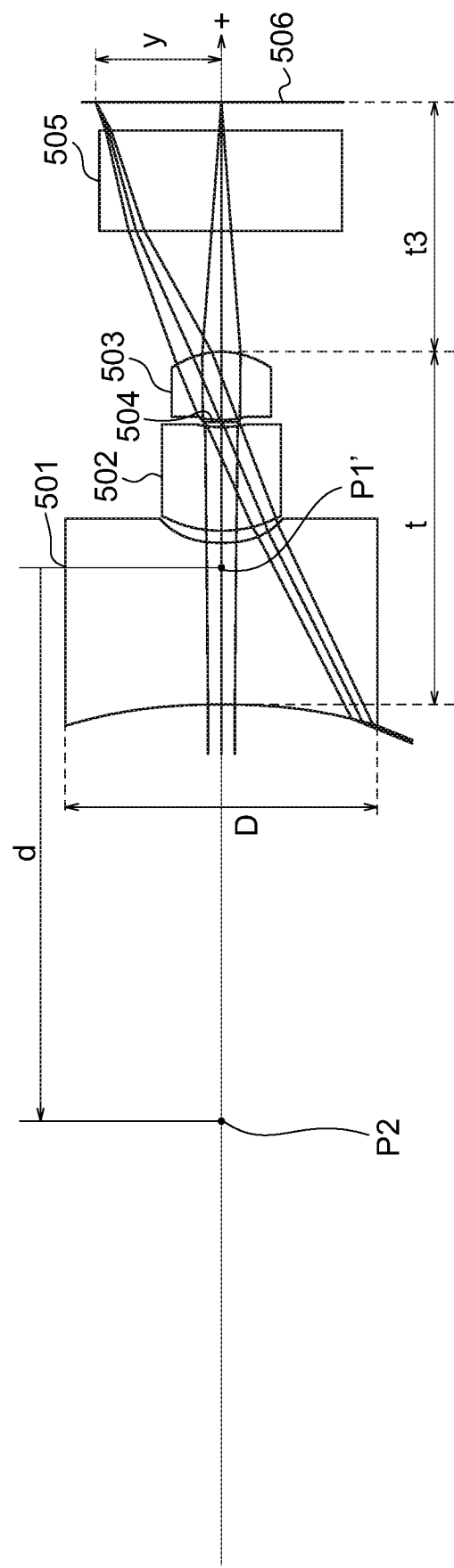
FIG. 13 shows a layout of the imaging optical system according to Example 5.

FIG. 13 shows a layout of the imaging optical system according to Example 5. The imaging optical system includes a first lens 501 having a negative refractive power, a second lens 502 having a positive refractive power, an aperture stop 504 and a third lens 503 having a positive refractive power, which are arranged from the object side to the image side. Light beams that pass through the above-described lenses pass through an optical member 505 and are focused on an image plane 506. The optical member 505 is a cover glass for a sensor or the like. FIG. 13 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from the surface of the object that is 15 mm distant from the first lens along the optical axis.

Table 9 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 501, the image-side surface of the first lens 501, the object-side surface of the second lens 502 and the image-side surface of the second lens 502. Surface 6 to surface 9 respectively represent the object-side surface of the third lens 503, the image-side surface of the third lens 503, the object-side surface of the plate 505 and the image-side surface of the plate 505. Radius of curvature in the line of object represents radius of curvature of the object surface, and "infinity" shows that the object surface is a plane that is perpendicular to the optical axis. Space in the line of object represents distance from the object surface to the object-side surface of the first lens 501. In the line of surface 1, radius of curvature represents signed radius of curvature at the center of curvature of the object-side surface of the first lens 501 (R of Expression (7)), space represents thickness of the first lens 501, refractive index represents refractive index of the material of the first lens 501, Abbe constant represents Abbe constant of the material of the first lens 501 and k represents the conic constant of Expression (7) of the object-side surface of the first lens 501. In the line of surface 2, radius of curvature represents signed radius of curvature at the center of curvature of the image-side surface of the first lens 501 (R of Expression (7)), space represents the space between the image-side surface of the first lens 501 and the object-side surface of the second lens 502 and k represents the conic constant of Expression (7) of the image-side surface of the first lens 501. Ditto with the succeeding lines.

TABLE 9

| # | Radius of curvature | Space | Refractive index | Abbe constant | K |
|---|---|---|---|---|---|
| Object | Infinity | 1.50E+01 | | | 0.00000E+00 |
| 1 | −2.37E+00 | 6.46E−01 | 1.5094 | 55.9 | 0.00000E+00 |
| 2 | 4.18E−01 | 5.51E−02 | | | 1.99930E−01 |
| 3 | 5.99E−01 | 4.14E−01 | 1.6141 | 25.3 | 2.86716E−01 |
| 4 | 4.97E−01 | 1.72E−02 | | | 0.00000E+00 |
| Aperture stop | Infinity | 1.00E−02 | | | 0.00000E+00 |
| 6 | 4.91E−01 | 2.78E−01 | 1.5312 | 56.0 | 0.00000E+00 |
| 7 | −3.47E−01 | 4.95E−01 | | | −9.63864E−02 |
| 8 | Infinity | 4.05E−01 | 1.5168 | 64.2 | 0.00000E+00 |
| 9 | Infinity | 1.00E−01 | | | 0.00000E+00 |

Table 10 shows aspheric coefficients of Expression (7) for surface 1 to surface 4 and surface 6 to surface 9.

TABLE 10

| # | A2 | A4 | A6 | A8 | A10 |
|---|---|---|---|---|---|
| Object | 0.00000E+00 | 0.00000E+00 | 0.00000E+00 | 0.00000E+00 | 0.00000E+00 |
| 1 | 0.00000E+00 | −4.84702E−03 | 0.00000E+00 | 0.00000E+00 | 0.00000E+00 |
| 2 | 0.00000E+00 | 7.04131E−01 | 4.17560E+00 | 1.62611E+02 | 0.00000E+00 |
| 3 | 0.00000E+00 | 9.89624E−02 | 2.87921E+00 | 1.55383E+02 | 0.00000E+00 |
| 4 | 0.00000E+00 | −9.11152E−01 | 2.82214E+01 | 1.11159E+04 | 0.00000E+00 |
| Aperture stop | 0.00000E+00 | 0.00000E+00 | 0.00000E+00 | 0.00000E+00 | 0.00000E+00 |
| 6 | 0.00000E+00 | −5.44029E+00 | −4.53114E+01 | 9.46614E+03 | 0.00000E+00 |
| 7 | 0.00000E+00 | 5.31601E−01 | −4.62430E+00 | 3.50228E+02 | 0.00000E+00 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

Figure 14:
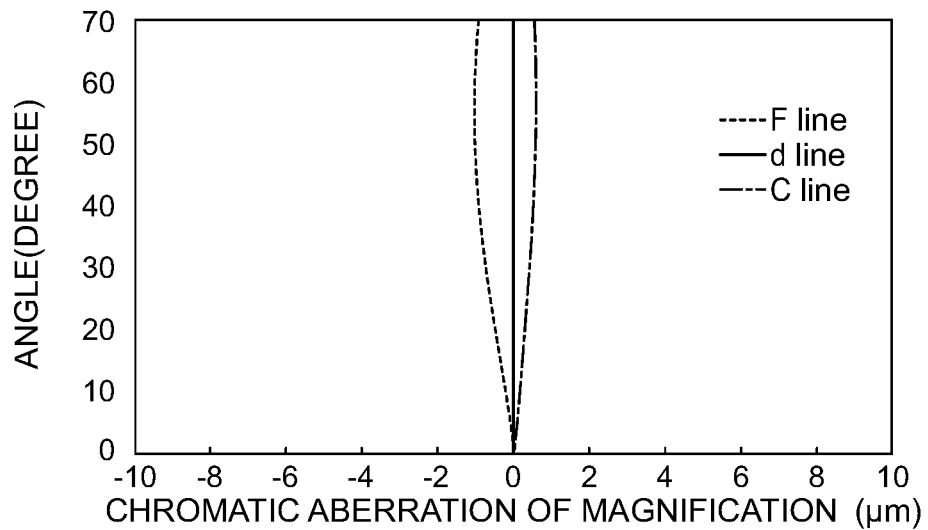
FIG. 14 shows chromatic aberrations of magnification of the imaging optical system according to Example 5.

FIG. 14 shows chromatic aberrations of magnification of the imaging optical system according to Example 5. The horizontal axis of FIG. 14 indicates chromatic aberrations of magnification of the F line and the C line with respect to the d line. The vertical axis of FIG. 14 indicates angle of the principal ray to the optical axis of a light beam that enters the imaging optical system. The maximum value of angle of the vertical axis corresponds to the half value of the angle of view.

Figure 15:
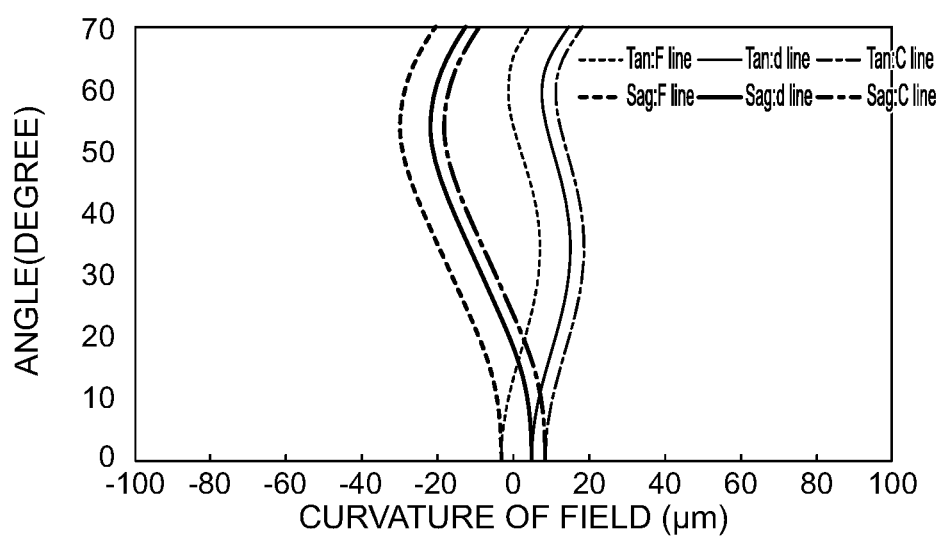
FIG. 15 shows curvature of field of the imaging optical system according to Example 5.

FIG. 15 shows curvature of field of the imaging optical system according to Example 5. The horizontal axis of FIG. 15 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 15 indicates angle of the principal ray to the optical axis of a light beam that enters the imaging optical system. The maximum value of angle of the vertical axis corresponds to the half value of the angle of view.

Example 6

Figure 16:
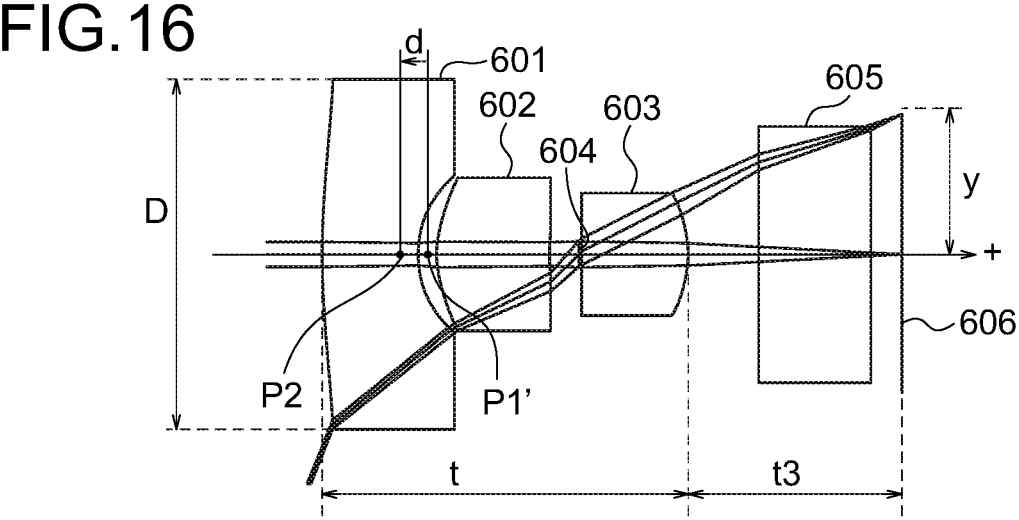
FIG. 16 shows a layout of the imaging optical system according to Example 6.

FIG. 16 shows a layout of the imaging optical system according to Example 6. The imaging optical system includes a first lens 601 having a negative refractive power, a second lens 602 having a positive refractive power, an aperture stop 604 and a third lens 603 having a positive refractive power, which are arranged from the object side to the image side. Light beams that pass through the above-described lenses pass through an optical member 605 and are focused on an image plane 606. The optical member 605 is a cover glass for a sensor or the like. FIG. 16 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from the surface of the object that is 15 mm distant from the first lens along the optical axis.

Table 11 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 601, the image-side surface of the first lens 601, the object-side surface of the second lens 602 and the image-side surface of the second lens 602. Surface 6 to surface 9 respectively represent the object-side surface of the third lens 603, the image-side surface of the third lens 603, the object-side surface of the plate 605 and the image-side surface of the plate 605. Radius of curvature in the line of object represents radius of curvature of the object surface, and "infinity" shows that the object surface is a plane that is perpendicular to the optical axis. Space in the line of object represents distance from the object surface to the object-side surface of the first lens 601. In the line of surface 1, radius of curvature represents signed radius of curvature at the center of curvature of the object-side surface of the first lens 601 (R of Expression (7)), space represents thickness of the first lens 601, refractive index represents refractive index of the material of the first lens 601, Abbe constant represents Abbe constant of the material of the first lens 601 and k represents the conic constant of Expression (7) of the object-side surface of the first lens 601. In the line of surface 2, radius of curvature represents signed radius of curvature at the center of curvature of the image-side surface of the first lens 601 (R of Expression (7)), space represents the space between the image-side surface of the first lens 601 and the object-side surface of the second lens 602 and k represents the conic constant of Expression (7) of the image-side surface of the first lens 601. Ditto with the succeeding lines.

TABLE 11

| # | Radius of curvature | Space | Refractive index | Abbe constant | K |
|---|---|---|---|---|---|
| Object | Infinity | 1.50E+01 | | | 0.00000E+00 |
| 1 | 4.15E+00 | 3.44E−01 | 1.5312 | 56.0 | 0.00000E+00 |
| 2 | 4.37E−01 | 6.45E−02 | | | 1.03807E+00 |
| 3 | 4.17E−01 | 4.06E−01 | 1.6141 | 25.3 | −3.58914E−01 |
| 4 | 1.05E+00 | 1.05E−01 | | | 0.00000E+00 |
| Aperture stop | Infinity | 1.00E−02 | | | 0.00000E+00 |
| 6 | 8.36E−01 | 3.84E−01 | 1.5312 | 56.0 | 0.00000E+00 |
| 7 | −5.31E−01 | 2.50E−01 | | | 6.87836E−01 |
| 8 | Infinity | 4.05E−01 | 1.5168 | 64.2 | 0.00000E+00 |
| 9 | Infinity | 1.00E−01 | | | 0.00000E+00 |

Table 12 shows aspheric coefficients of Expression (7) for surface 1 to surface 4 and surface 6 to surface 9.

TABLE 12

| # | A2 | A4 | A6 | A8 | A10 |
|---|---|---|---|---|---|
| Object | 0.00000E+00 | 0.00000E+00 | 0.00000E+00 | 0.00000E+00 | 0.00000E+00 |
| 1 | 0.00000E+00 | −7.27996E−02 | −6.94666E−02 | −9.01558E−03 | 0.00000E+00 |
| 2 | 0.00000E+00 | −1.45350E+00 | −6.07744E+00 | −3.16691E+01 | 0.00000E+00 |
| 3 | 0.00000E+00 | −3.38606E+00 | −1.44576E+01 | 1.61369E+01 | 0.00000E+00 |
| 4 | 0.00000E+00 | −2.33153E+01 | 4.56523E+02 | −6.35747E+03 | 0.00000E+00 |
| Aperture stop | 0.00000E+00 | 0.00000E+00 | 0.00000E+00 | 0.00000E+00 | 0.00000E+00 |
| 6 | 0.00000E+00 | −4.73363E−01 | −7.94867E+03 | 1.52276E+06 | 0.00000E+00 |
| 7 | 0.00000E+00 | −5.93511E+00 | 2.12821E+01 | 3.74694E+01 | 0.00000E+00 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

Figure 17:
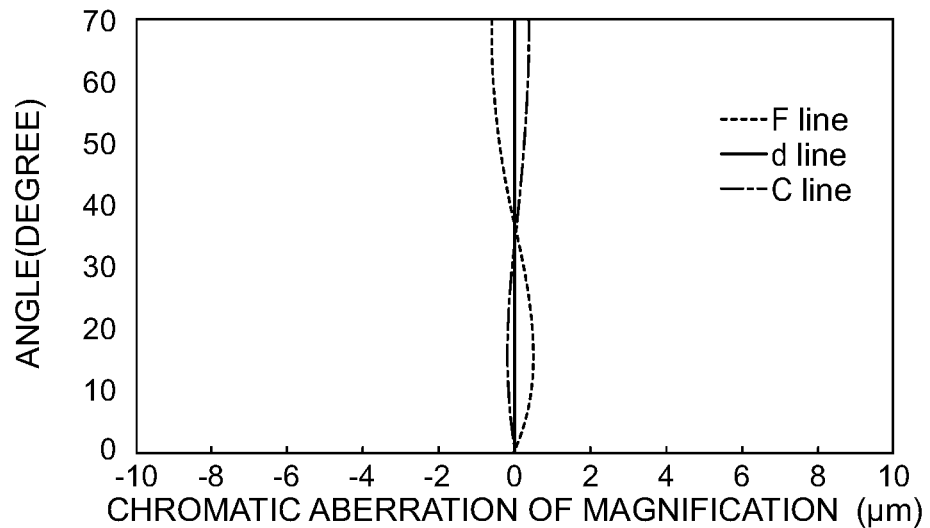
FIG. 17 shows chromatic aberrations of magnification of the imaging optical system according to Example 6.

FIG. 17 shows chromatic aberrations of magnification of the imaging optical system according to Example 6. The horizontal axis of FIG. 17 indicates chromatic aberrations of magnification of the F line and the C line with respect to the d line. The vertical axis of FIG. 17 indicates angle of the principal ray to the optical axis of a light beam that enters the imaging optical system. The maximum value of angle of the vertical axis corresponds to the half value of the angle of view.

Figure 18:
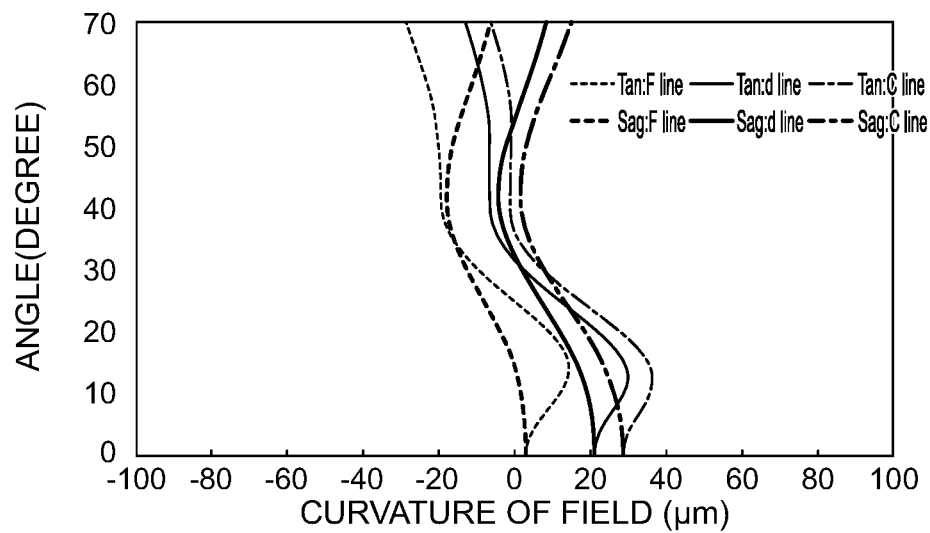
FIG. 18 shows curvature of field of the imaging optical system according to Example 6.

FIG. 18 shows curvature of field of the imaging optical system according to Example 6. The horizontal axis of FIG. 18 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 18 indicates angle of the principal ray to the optical axis of a light beam that enters the imaging optical system. The maximum value of angle of the vertical axis corresponds to the half value of the angle of view.

Example 7

Figure 19:
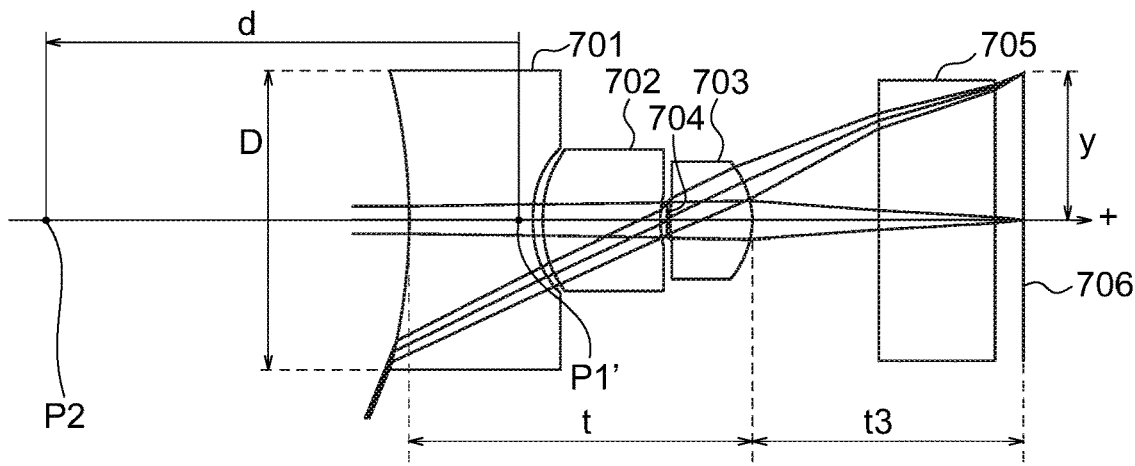
FIG. 19 shows a layout of the imaging optical system according to Example 7.

FIG. 19 shows a layout of the imaging optical system according to Example 7. The imaging optical system includes a first lens 701 having a negative refractive power, a second lens 702 having a positive refractive power, an aperture stop 704 and a third lens 703 having a positive refractive power, which are arranged from the object side to the image side. Light beams that pass through the above-described lenses pass through an optical member 705 and are focused on an image plane 706. The optical member 705 is a cover glass for a sensor or the like. FIG. 19 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from the surface of the object that is 15 mm distant from the first lens along the optical axis.

Table 13 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 701, the image-side surface of the first lens 701, the object-side surface of the second lens 702 and the image-side surface of the second lens 702. Surface 6 to surface 9 respectively represent the object-side surface of the third lens 703, the image-side surface of the third lens 703, the object-side surface of the plate 705 and the image-side surface of the plate 705. Radius of curvature in the line of object represents radius of curvature of the object surface, and "infinity" shows that the object surface is a plane that is perpendicular to the optical axis. Space in the line of object represents distance from the object surface to the object-side surface of the first lens 701. In the line of surface 1, radius of curvature represents signed radius of curvature at the center of curvature of the object-side surface of the first lens 701 (R of Expression (7)), space represents thickness of the first lens 701, refractive index represents refractive index of the material of the first lens 701, Abbe constant represents Abbe constant of the material of the first lens 701 and k represents the conic constant of Expression (7) of the object-side surface of the first lens 701. In the line of surface 2, radius of curvature represents signed radius of curvature at the center of curvature of the image-side surface of the first lens 701 (R of Expression (7)), space represents the space between the image-side surface of the first lens 701 and the object-side surface of the second lens 702 and k represents the conic constant of Expression (7) of the image-side surface of the first lens 701. Ditto with the succeeding lines.

TABLE 13

| # | Radius of curvature | Space | Refractive index | Abbe constant | K |
|---|---|---|---|---|---|
| Object | Infinity | 1.50E+01 | | | 0.00000E+00 |
| 1 | −1.91E+00 | 4.30E−01 | 1.5312 | 56.0 | 0.00000E+00 |
| 2 | 5.15E−01 | 2.93E−02 | | | 1.98047E+00 |
| 3 | 5.21E−01 | 4.07E−01 | 1.6141 | 25.3 | 1.91268E+00 |
| 4 | 4.46E−01 | 2.22E−02 | | | 0.00000E+00 |
| Aperture stop | Infinity | 1.00E−02 | | | 0.00000E+00 |
| 6 | 6.34E−01 | 2.85E−01 | 1.5312 | 56.0 | 0.00000E+00 |
| 7 | −3.06E−01 | 4.30E−01 | | | −7.17388E−02 |
| 8 | Infinity | 4.05E−01 | 1.5168 | 64.2 | 0.00000E+00 |
| 9 | Infinity | 1.00E−01 | | | 0.00000E+00 |

Table 14 shows aspheric coefficients of Expression (7) for surface 1 to surface 4 and surface 6 to surface 9.

TABLE 14

| # | A2 | A4 | A6 | A8 | A10 |
|---|---|---|---|---|---|
| Object | 0.00000E+00 | 0.00000E+00 | 0.00000E+00 | 0.00000E+00 | 0.00000E+00 |
| 1 | 0.00000E+00 | 0.00000E+00 | 0.00000E+00 | 0.00000E+00 | 0.00000E+00 |
| 2 | 0.00000E+00 | 0.00000E+00 | 0.00000E+00 | 0.00000E+00 | 0.00000E+00 |
| 3 | 0.00000E+00 | 0.00000E+00 | 0.00000E+00 | 0.00000E+00 | 0.00000E+00 |
| 4 | 0.00000E+00 | 0.00000E+00 | 0.00000E+00 | 0.00000E+00 | 0.00000E+00 |
| Aperture stop | 0.00000E+00 | 0.00000E+00 | 0.00000E+00 | 0.00000E+00 | 0.00000E+00 |
| 6 | 0.00000E+00 | 0.00000E+00 | 0.00000E+00 | 0.00000E+00 | 0.00000E+00 |
| 7 | 0.00000E+00 | 0.00000E+00 | 0.00000E+00 | 0.00000E+00 | 0.00000E+00 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

Figure 20:
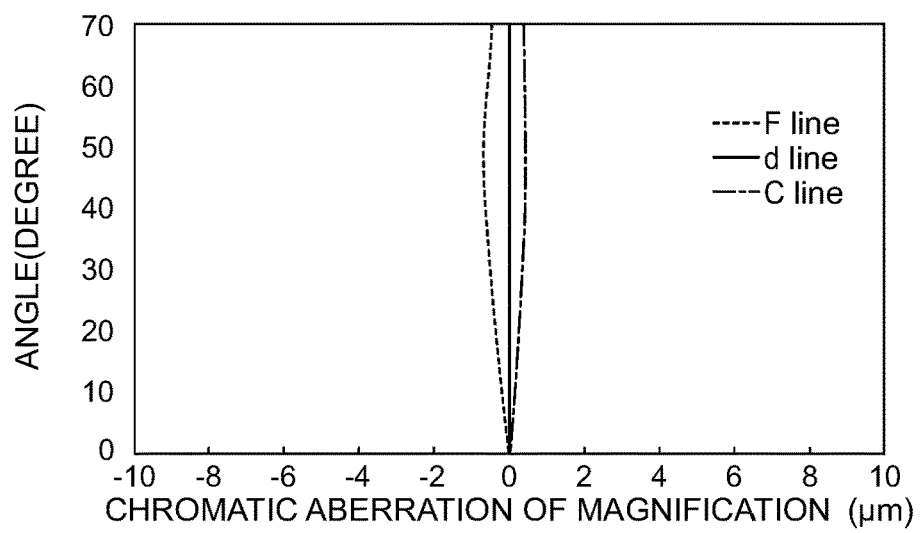
FIG. 20 shows chromatic aberrations of magnification of the imaging optical system according to Example 7.

FIG. 20 shows chromatic aberrations of magnification of the imaging optical system according to Example 7. The horizontal axis of FIG. 20 indicates chromatic aberrations of magnification of the F line and the C line with respect to the d line. The vertical axis of FIG. 20 indicates angle of the principal ray to the optical axis of a light beam that enters the imaging optical system. The maximum value of angle of the vertical axis corresponds to the half value of the angle of view.

Figure 21:
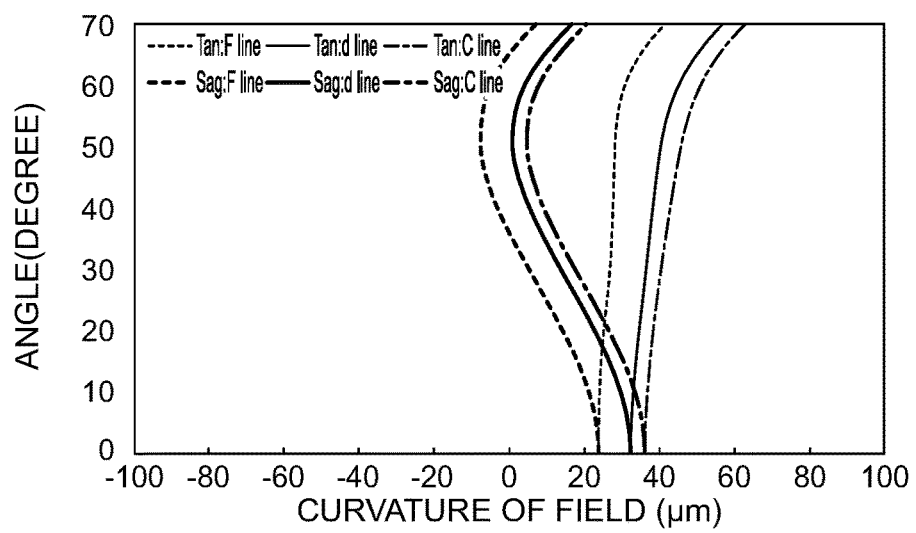
FIG. 21 shows curvature of field of the imaging optical system according to Example 7.

FIG. 21 shows curvature of field of the imaging optical system according to Example 7. The horizontal axis of FIG. 21 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 21 indicates angle of the principal ray to the optical axis of a light beam that enters the imaging optical system. The maximum value of angle of the vertical axis corresponds to the half value of the angle of view.

Example 8

Figure 22:
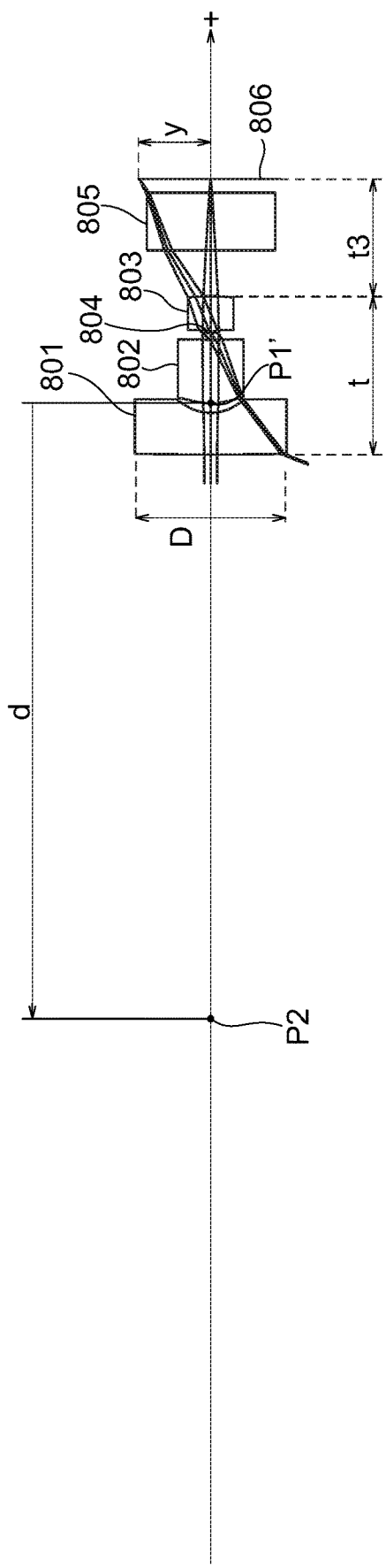
FIG. 22 shows a layout of the imaging optical system according to Example 8.

FIG. 22 shows a layout of the imaging optical system according to Example 8. The imaging optical system includes a first lens 801 having a negative refractive power, a second lens 802 having a positive refractive power, an aperture stop 804 and a third lens 803 having a positive refractive power, which are arranged from the object side to the image side. Light beams that pass through the above-described lenses pass through an optical member 805 and are focused on an image plane 806. The optical member 805 is a cover glass for a sensor or the like. FIG. 22 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from the surface of the object that is 15 mm distant from the first lens along the optical axis.

Table 15 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 801, the image-side surface of the first lens 801, the object-side surface of the second lens 802 and the image-side surface of the second lens 802. Surface 6 to surface 9 respectively represent the object-side surface of the third lens 803, the image-side surface of the third lens 803, the object-side surface of the plate 805 and the image-side surface of the plate 805. Radius of curvature in the line of object represents radius of curvature of the object surface, and "infinity" shows that the object surface is a plane that is perpendicular to the optical axis. Space in the line of object represents distance from the object surface to the object-side surface of the first lens 801. In the line of surface 1, radius of curvature represents signed radius of curvature at the center of curvature of the object-side surface of the first lens 801 (R of Expression (7)), space represents thickness of the first lens 801, refractive index represents refractive index of the material of the first lens 801, Abbe constant represents Abbe constant of the material of the first lens 801 and k represents the conic constant of Expression (7) of the object-side surface of the first lens 801. In the line of surface 2, radius of curvature represents signed radius of curvature at the center of curvature of the image-side surface of the first lens 801 (R of Expression (7)), space represents the space between the image-side surface of the first lens 801 and the object-side surface of the second lens 802 and k represents the conic constant of Expression (7) of the image-side surface of the first lens 801. Ditto with the succeeding lines.

TABLE 15

| # | Radius of curvature | Space | Refractive index | Abbe constant | K |
|---|---|---|---|---|---|
| Object | Infinity | 1.50E+01 | | | 0.00000E+00 |
| 1 | Infinity | 2.97E−01 | 1.5312 | 56.0 | 0.00000E+00 |
| 2 | 4.08E−01 | 6.61E−02 | | | 6.42301E−01 |
| 3 | 5.67E−01 | 4.50E−01 | 1.6141 | 25.3 | −1.50437E+00 |
| 4 | 4.32E−01 | 5.03E−02 | | | 0.00000E+00 |
| Aperture stop | Infinity | 1.00E−02 | | | 0.00000E+00 |
| 6 | 2.31E−01 | 2.50E−01 | 1.5312 | 56.0 | 0.00000E+00 |
| 7 | −1.04E+00 | 3.22E−01 | | | −1.50000E+00 |
| 8 | Infinity | 4.05E−01 | 1.5168 | 64.2 | 0.00000E+00 |
| 9 | Infinity | 1.00E−01 | | | 0.00000E+00 |

Table 16 shows aspheric coefficients of Expression (7) for surface 1 to surface 4 and surface 6 to surface 9.

TABLE 16

| # | A2 | A4 | A6 | A8 | A10 |
|---|---|---|---|---|---|
| Object | 0.00000E+00 | 0.00000E+00 | 0.00000E+00 | 0.00000E+00 | 0.00000E+00 |
| 1 | 0.00000E+00 | 0.00000E+00 | 0.00000E+00 | 0.00000E+00 | 0.00000E+00 |
| 2 | 0.00000E+00 | 8.52198E+00 | −1.43769E+02 | −6.48423E+00 | 1.56548E+03 |
| 3 | 0.00000E+00 | 6.03273E+00 | −2.43533E+02 | 8.15699E+02 | 3.05956E+02 |
| 4 | 0.00000E+00 | −2.74392E+01 | −4.04452E+03 | 2.14129E+05 | 1.55344E+06 |
| Aperture stop | 0.00000E+00 | 0.00000E+00 | 0.00000E+00 | 0.00000E+00 | 0.00000E+00 |
| 6 | 0.00000E+00 | −6.05722E+01 | 2.95632E+03 | −1.41390E+04 | −4.38597E+06 |
| 7 | 0.00000E+00 | −2.59252E+00 | 1.10472E+02 | 2.15127E+03 | 1.77583E+04 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

Figure 23:
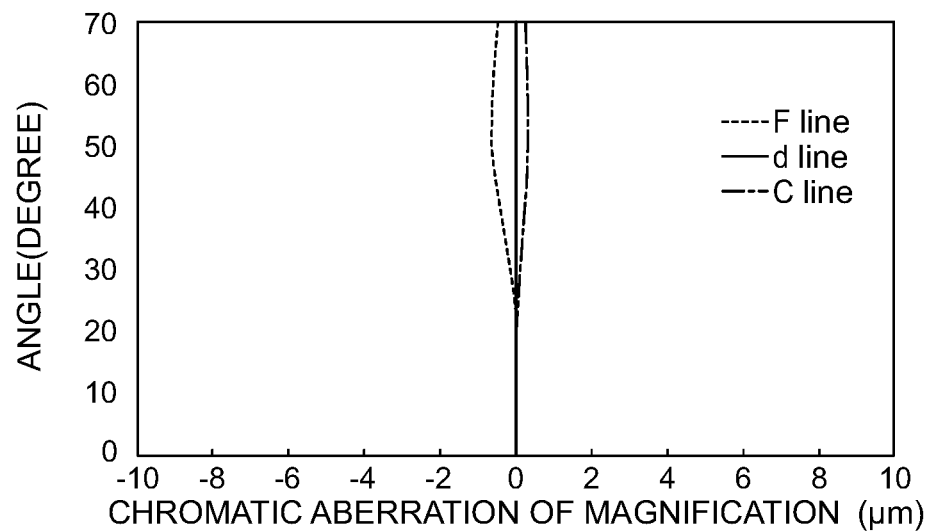
FIG. 23 shows chromatic aberrations of magnification of the imaging optical system according to Example 8.

FIG. 23 shows chromatic aberrations of magnification of the imaging optical system according to Example 8. The horizontal axis of FIG. 23 indicates chromatic aberrations of magnification of the F line and the C line with respect to the d line. The vertical axis of FIG. 23 indicates angle of the principal ray to the optical axis of a light beam that enters the imaging optical system. The maximum value of angle of the vertical axis corresponds to the half value of the angle of view.

Figure 24:
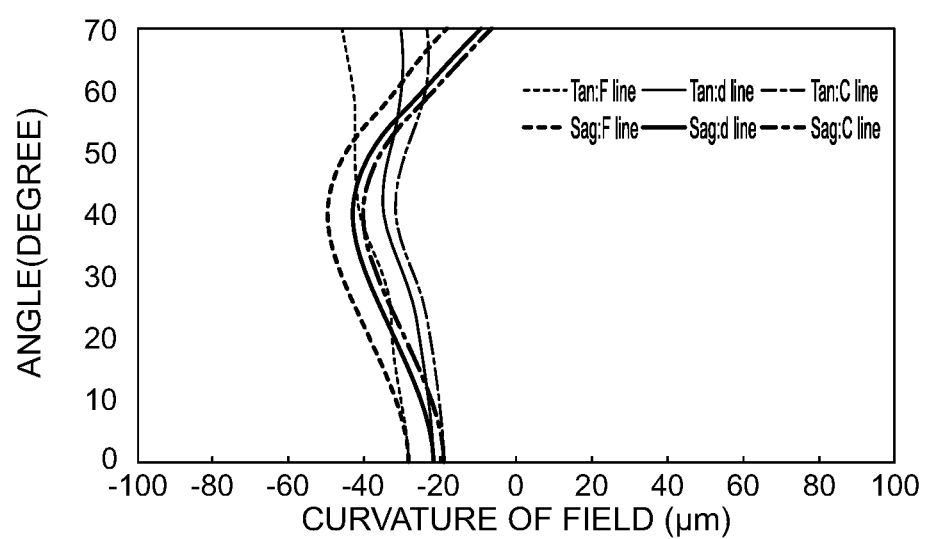
FIG. 24 shows curvature of field of the imaging optical system according to Example 8.

FIG. 24 shows curvature of field of the imaging optical system according to Example 8. The horizontal axis of FIG. 24 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 24 indicates angle of the principal ray to the optical axis of a light beam that enters the imaging optical system. The maximum value of angle of the vertical axis corresponds to the half value of the angle of view.

Example 9

Figure 25:
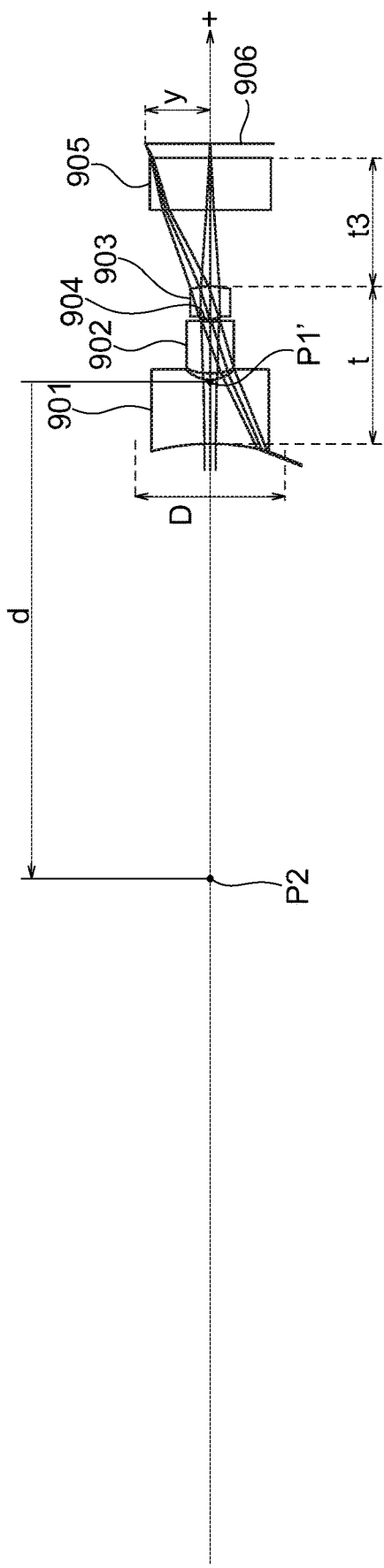
FIG. 25 shows a layout of the imaging optical system according to Example 9.

FIG. 25 shows a layout of the imaging optical system according to Example 9. The imaging optical system includes a first lens 901 having a negative refractive power, a second lens 902 having a positive refractive power, an aperture stop 904 and a third lens 903 having a positive refractive power, which are arranged from the object side to the image side. Light beams that pass through the above-described lenses pass through an optical member 905 and are focused on an image plane 906. The optical member 905 is a cover glass for a sensor or the like. FIG. 25 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from the surface of the object that is 15 mm distant from the first lens along the optical axis.

Table 17 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 901, the image-side surface of the first lens 901, the object-side surface of the second lens 902 and the image-side surface of the second lens 902. Surface 6 to surface 9 respectively represent the object-side surface of the third lens 903, the image-side surface of the third lens 903, the object-side surface of the plate 905 and the image-side surface of the plate 905. Radius of curvature in the line of object represents radius of curvature of the object surface, and "infinity" shows that the object surface is a plane that is perpendicular to the optical axis. Space in the line of object represents distance from the object surface to the object-side surface of the first lens 901. In the line of surface 1, radius of curvature represents signed radius of curvature at the center of curvature of the object-side surface of the first lens 901 (R of Expression (7)), space represents thickness of the first lens 901, refractive index represents refractive index of the material of the first lens 901, Abbe constant represents Abbe constant of the material of the first lens 901 and k represents the conic constant of Expression (7) of the object-side surface of the first lens 901. In the line of surface 2, radius of curvature represents signed radius of curvature at the center of curvature of the image-side surface of the first lens 901 (R of Expression (7)), space represents the space between the image-side surface of the first lens 901 and the object-side surface of the second lens 902 and k represents the conic constant of Expression (7) of the image-side surface of the first lens 901. Ditto with the succeeding lines.

TABLE 17

| # | Radius of curvature | Space | Refractive index | Abbe constant | K |
|---|---|---|---|---|---|
| Object | Infinity | 1.50E+01 | | | 0.00000E+00 |
| 1 | −2.00E+00 | 4.94E−01 | 1.5312 | 56.0 | 3.96099E+00 |
| 2 | 3.00E−01 | 4.99E−02 | | | −2.32051E−01 |
| 3 | 6.70E−01 | 4.02E−01 | 1.6141 | 25.3 | 4.55307E+00 |
| 4 | 5.61E−01 | 1.29E−02 | | | 0.00000E+00 |
| Aperture stop | Infinity | 1.00E−02 | | | 0.00000E+00 |
| 6 | 2.95E−01 | 2.50E−01 | 1.5312 | 56.0 | 4.18127E+00 |
| 7 | −5.03E−01 | 5.90E−01 | | | −1.21225E+00 |
| 8 | Infinity | 4.05E−01 | 1.5168 | 64.2 | 0.00000E+00 |
| 9 | Infinity | 1.00E−01 | | | 0.00000E+00 |

Table 18 shows aspheric coefficients of Expression (7) for surface 1 to surface 4 and surface 6 to surface 9.

TABLE 18

| # | A2 | A4 | A6 | A8 | A10 |
|---|---|---|---|---|---|
| Object | 0.00000E+00 | 0.00000E+00 | 0.00000E+00 | 0.00000E+00 | 0.00000E+00 |
| 1 | 0.00000E+00 | −3.47273E−01 | 7.15006E−01 | 0.00000E+00 | 0.00000E+00 |
| 2 | 0.00000E+00 | 7.31812E+00 | 5.25145E+01 | 0.00000E+00 | 0.00000E+00 |
| 3 | 0.00000E+00 | 4.81962E+00 | −1.23638E+01 | 1.57127E+02 | 0.00000E+00 |
| 4 | 0.00000E+00 | 2.70188E+00 | −8.44187E+02 | 6.15800E+04 | 0.00000E+00 |
| Aperture stop | 0.00000E+00 | 0.00000E+00 | 0.00000E+00 | 0.00000E+00 | 0.00000E+00 |
| 6 | 0.00000E+00 | −2.74171E+01 | 7.84544E+01 | −9.96879E+04 | 0.00000E+00 |
| 7 | 0.00000E+00 | 4.55581E+00 | 3.88997E+01 | 3.61150E+03 | 0.00000E+00 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

Figure 26:
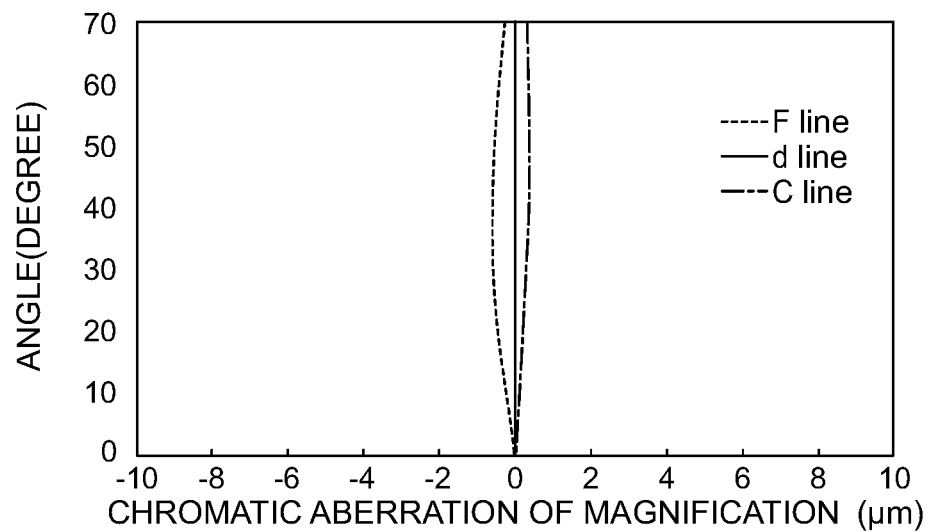
FIG. 26 shows chromatic aberrations of magnification of the imaging optical system according to Example 9.

FIG. 26 shows chromatic aberrations of magnification of the imaging optical system according to Example 9. The horizontal axis of FIG. 26 indicates chromatic aberrations of magnification of the F line and the C line with respect to the d line. The vertical axis of FIG. 26 indicates angle of the principal ray to the optical axis of a light beam that enters the imaging optical system. The maximum value of angle of the vertical axis corresponds to the half value of the angle of view.

Figure 27:
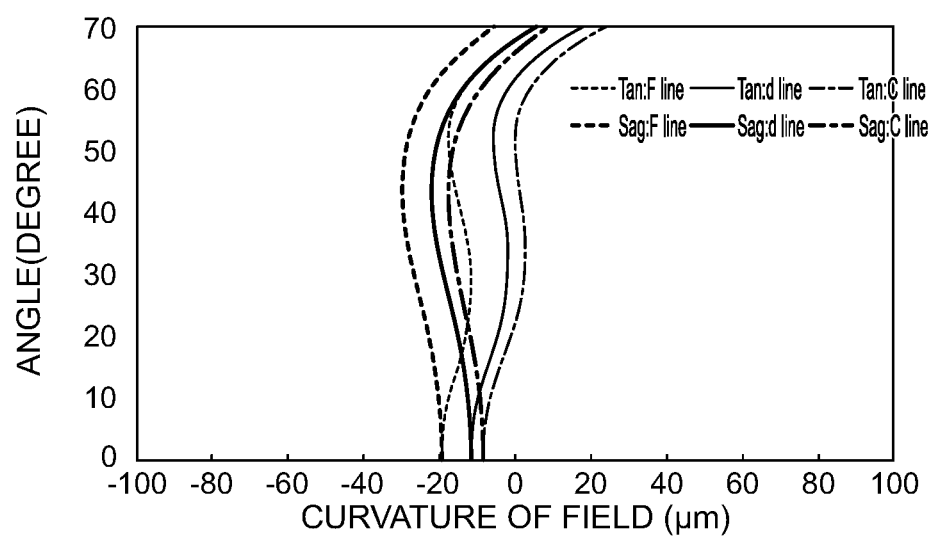
FIG. 27 shows curvature of field of the imaging optical system according to Example 9.

FIG. 27 shows curvature of field of the imaging optical system according to Example 8. The horizontal axis of FIG. 27 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 27 indicates angle of the principal ray to the optical axis of a light beam that enters the imaging optical system. The maximum value of angle of the vertical axis corresponds to the half value of the angle of view.

Example 10

Figure 28:
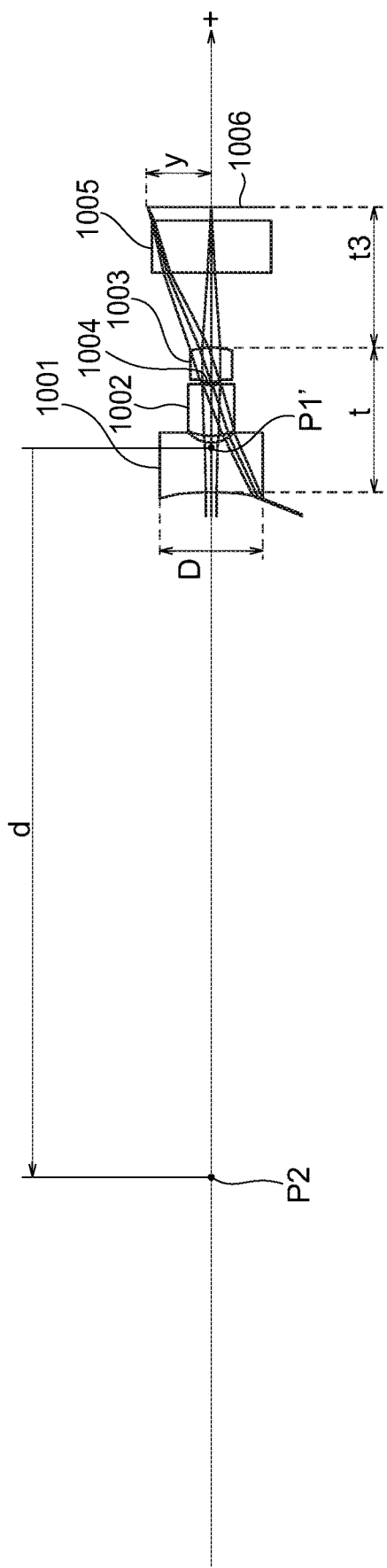
FIG. 28 shows a layout of the imaging optical system according to Example 10.

FIG. 28 shows a layout of the imaging optical system according to Example 10. The imaging optical system includes a first lens 1001 having a negative refractive power, a second lens 1002 having a positive refractive power, an aperture stop 1004 and a third lens 1003 having a positive refractive power, which are arranged from the object side to the image side. Light beams that pass through the above-described lenses pass through an optical member 1005 and are focused on an image plane 1006. The optical member 1005 is a cover glass for a sensor or the like. FIG. 25 shows the optical path of a light beam including the principal ray that travels parallel to the optical axis from a surface of the object that is 15 mm distant from the first lens along the optical axis and the optical path of a light beam including the principal ray that travels at the angle of the half value of the angle of view to the optical axis from surface of the object that is 15 mm distant from the first lens along the optical axis.

Table 19 shows shapes and properties of materials of optical elements including the first lens, the second lens and the third lens and spaces between the optical elements. The numbers in the leftmost column in the table represent surface numbers. Surface 1 to surface 4 respectively represent the object-side surface of the first lens 1001, the image-side surface of the first lens 1001, the object-side surface of the second lens 1002 and the image-side surface of the second lens 1002. Surface 6 to surface 9 respectively represent the object-side surface of the third lens 1003, the image-side surface of the third lens 1003, the object-side surface of the plate 1005 and the image-side surface of the plate 1005. Radius of curvature in the line of object represents radius of curvature of the object surface, and "infinity" shows that the object surface is a plane that is perpendicular to the optical axis. Space in the line of object represents distance from the object surface to the object-side surface of the first lens 1001. In the line of surface 1, radius of curvature represents signed radius of curvature at the center of curvature of the object-side surface of the first lens 1001 (R of Expression (7)), space represents thickness of the first lens 1001, refractive index represents refractive index of the material of the first lens 1001, Abbe constant represents Abbe constant of the material of the first lens 1001 and k represents the conic constant of Expression (7) of the object-side surface of the first lens 1001. In the line of surface 2, radius of curvature represents signed radius of curvature at the center of curvature of the image-side surface of the first lens 1001 (R of Expression (7)), space represents the space between the image-side surface of the first lens 1001 and the object-side surface of the second lens 1002 and k represents the conic constant of Expression (7) of the image-side surface of the first lens 1001. Ditto with the succeeding lines.

TABLE 19

| # | Radius of curvature | Space | Refractive index | Abbe constant | K |
| --- | --- | --- | --- | --- | --- |
| Object | Infinity | 1.50E+01 | | | 0.00000E+00 |
| 1 | −1.75E+00 | 3.86E−01 | 1.5312 | 56.0 | 0.00000E+00 |
| 2 | 3.01E−01 | 5.10E−02 | | | −1.61707E−01 |
| 3 | 6.77E−01 | 4.00E−01 | 1.6141 | 25.3 | −3.33327E−01 |
| 4 | 5.55E−01 | 1.25E−02 | | | 0.00000E+00 |
| Aperture stop | Infinity | 1.00E−02 | | | 0.00000E+00 |
| 6 | 2.96E−01 | 2.69E−01 | 1.5312 | 56.0 | 0.00000E+00 |
| 7 | −4.91E−01 | 5.85E−01 | | | −7.07649E−01 |
| 8 | Infinity | 4.05E−01 | 1.5168 | 64.2 | 0.00000E+00 |
| 9 | Infinity | 1.00E−01 | | | 0.00000E+00 |

Table 20 shows aspheric coefficients of Expression (7) for surface 1 to surface 4 and surface 6 to surface 9.

TABLE 20

| # | A2 | A4 | A6 | A8 | A10 |
| --- | --- | --- | --- | --- | --- |
| Object | 0.00000E+00 | 0.00000E+00 | 0.00000E+00 | 0.00000E+00 | 0.00000E+00 |
| 1 | 0.00000E+00 | −2.71834E−01 | 1.52366E−01 | 0.00000E+00 | 0.00000E+00 |
| 2 | 0.00000E+00 | 3.33200E+00 | 1.80652E+02 | 0.00000E+00 | 0.00000E+00 |
| 3 | 0.00000E+00 | 2.88348E+00 | 1.22197E+02 | −7.00087E−01 | 0.00000E+00 |
| 4 | 0.00000E+00 | −1.32208E+01 | 1.32659E+02 | 5.16522E+02 | 0.00000E+00 |
| Aperture stop | 0.00000E+00 | 0.00000E+00 | 0.00000E+00 | 0.00000E+00 | 0.00000E+00 |
| 6 | 0.00000E+00 | −1.81228E+01 | 2.40954E+02 | −1.79912E+02 | 0.00000E+00 |
| 7 | 0.00000E+00 | 2.26724E+00 | 8.39687E+01 | 4.75301E+01 | 0.00000E+00 |
| 8 | 0.00000E+00 | 0.00000E+00 | 0.00000E+00 | 0.00000E+00 | 0.00000E+00 |
| 9 | 0.00000E+00 | 0.00000E+00 | 0.00000E+00 | 0.00000E+00 | 0.00000E+00 |

Figure 29:
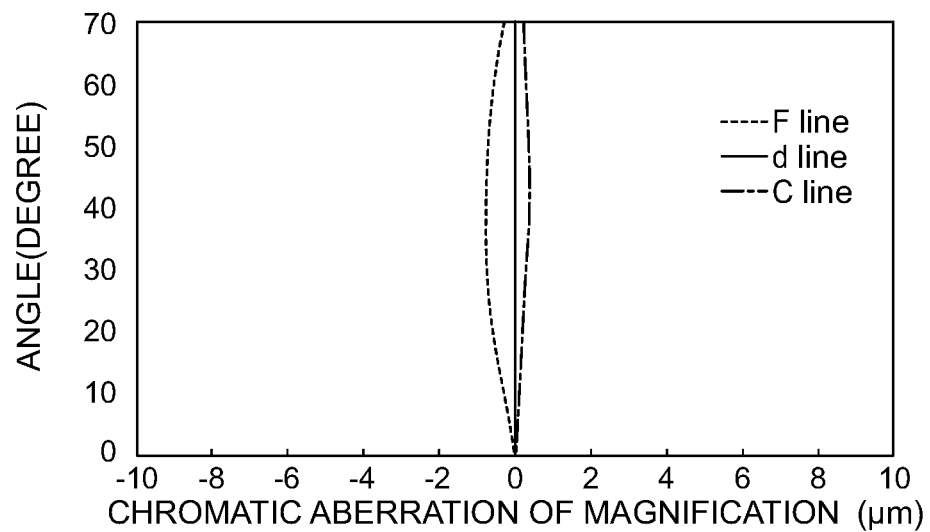
FIG. 29 shows chromatic aberrations of magnification of the imaging optical system according to Example 10.

FIG. 29 shows chromatic aberrations of magnification of the imaging optical system according to Example 10. The horizontal axis of FIG. 29 indicates chromatic aberrations of magnification of the F line and the C line with respect to the d line. The vertical axis of FIG. 29 indicates angle of the principal ray to the optical axis of a light beam that enters the imaging optical system. The maximum value of angle of the vertical axis corresponds to the half value of the angle of view.

Figure 30:
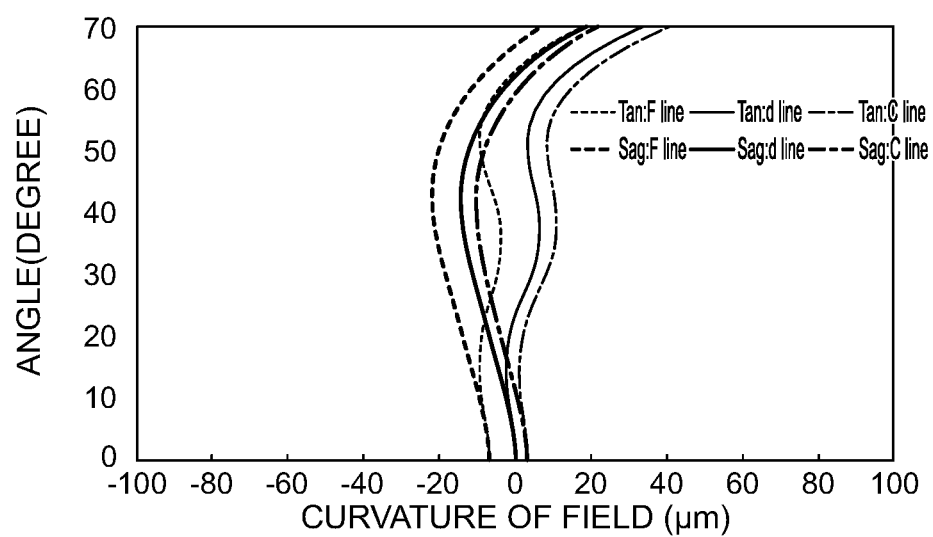
FIG. 30 shows curvature of field of the imaging optical system according to Example 10.

FIG. 30 shows curvature of field of the imaging optical system according to Example 10. The horizontal axis of FIG. 30 indicates positions defined in the optical-axis coordinate of tangential image surfaces and sagittal image surfaces of the F line, the d line and the C line. In the drawing, Tan represents tangential image surfaces, and Sag represents sagittal image surfaces. The vertical axis of FIG. 30 indicates angle of the principal ray to the optical axis of a light beam that enters the imaging optical system. The maximum value of angle of the vertical axis corresponds to the half value of the angle of view.

Summary of the Examples

Table 21 summarizes features of Example 1 to Example 10. In the table, the unit of length is millimeter, and the unit of angle is degree.

TABLE 21

|  | 2ω (°) | d | f12 | d/f12 | t | t3 | t3/t | D | y | 2 × y/D |
|---|---|---|---|---|---|---|---|---|---|---|
| Example 1 | 140 | −0.079 | −0.622 | 0.127 | 1.097 | 0.938 | 0.854 | 0.901 | 0.520 | 1.154 |
| Example 2 | 140 | −2.414 | −0.541 | 4.458 | 1.236 | 0.938 | 0.759 | 0.898 | 0.516 | 1.149 |
| Example 3 | 140 | −0.377 | −0.716 | 0.527 | 1.245 | 0.858 | 0.689 | 1.289 | 0.519 | 0.805 |
| Example 4 | 140 | −0.435 | −1.029 | 0.423 | 1.358 | 0.989 | 0.728 | 1.299 | 0.517 | 0.796 |
| Example 5 | 140 | −2.667 | −0.526 | 5.073 | 1.421 | 1.000 | 0.704 | 1.290 | 0.515 | 0.798 |
| Example 6 | 140 | −0.096 | −17.153 | 0.006 | 1.313 | 0.755 | 0.575 | 1.300 | 0.515 | 0.792 |
| Example 7 | 140 | −1.549 | −0.613 | 2.526 | 1.184 | 0.935 | 0.790 | 1.055 | 0.515 | 0.976 |
| Example 8 | 140 | −4.265 | −0.583 | 7.311 | 1.124 | 0.827 | 0.736 | 1.099 | 0.519 | 0.944 |
| Example 9 | 140 | −3.778 | −0.371 | 10.174 | 1.219 | 1.095 | 0.898 | 0.925 | 0.513 | 1.109 |
| Example 10 | 140 | −5.607 | −0.364 | 15.385 | 1.129 | 1.090 | 0.965 | 0.829 | 0.514 | 1.240 |

In the table, ω represents a half value of angle of view, and 2ω represents a value of angle of view. According to Table 21, all the examples satisfy Expression (1), Expression (2), Expression (3) and Expression (6). Examples 1 to 5 and Example 7 satisfy Expression (2)', and Example 1 satisfies Expression (2)''. Further, according to the tables of respective examples, all the examples satisfy Expression (4) and Expression (5).

According to the drawings of aberrations of respective examples, chromatic aberrations of magnification of the F line and the C line with respect to the d line of the imaging optical systems of most examples are in the range of ±1 micrometer, and curvatures of field shown by tangential image surfaces and sagittal image surfaces of the F line, the d line and the C line of the imaging optical systems of most examples are in the range of ±40 micrometers.

What is claimed is:

1. An imaging optical system comprising a first lens having a negative refractive power, a second lens having a positive refractive power, an aperture stop and a third lens having a positive refractive power, which are arranged from the object side to the image side, wherein when distance between the image-side principal point of the first lens and the object-side principal point of the second lens is represented by |d|, signed distance is represented by d=−|d| when the image-side principal point of the first lens is located closer to the image than the object-side principal point of the second lens, and the composite focal length of the first lens and the second lens is represented by f12, the relationships $d<0$ and $0.005<d/f12<16$ are established, and wherein when the common principal axis of the first lens, the second lens and the third lens is defined as the optical axis, distance between the point on the optical axis and on the image-side surface of the third lens and the image plane is represented by t3, and distance between the point on the optical axis and on the object-side surface of the first lens and the point on the optical axis and on the image-side surface of the third lens is represented by t, the relationship $t3/t>0.5$ is established.

2. An imaging optical system according to claim 1, wherein the relationship $0.1<d/f12<6$ is established.

3. An imaging optical system according to claim 1, wherein the relationship $0.12<d/f12<0.15$ is established.

4. An imaging optical system according to claim 1, wherein when the common principal axis of the first lens, the second lens and the third lens is defined as the optical axis, the point on the optical axis and on the object-side surface of the second lens is located closer to the object than the point on the image-side surface of the first lens, through which the outermost light ray of a light beam corresponding to the angle of view passes.

5. An imaging optical system according to claim 1, wherein when Abbe constant of the material of which the first lens is made is represented by ν1, Abbe constant of the material of which the second lens is made is represented by ν2 and Abbe constant of the material of which the third lens is made is represented by ν3, the relationships $\nu 1>\nu 2$ and $\nu 3>\nu 2$ are established.

6. An imaging optical system according to claim 1, wherein when image height of the light beam corresponding to the angle of view is represented by y, and the effective diameter of the first lens is represented by D, the relationship $0.75<2xy/D<1.25$ is established.

7. An imaging optical system according to claim 1 provided with an image sensor in the frontend portion of an insertion type endoscope or in a capsule type endoscope.

* * * * *